United States Patent
Gao et al.

(10) Patent No.: US 12,371,691 B2
(45) Date of Patent: Jul. 29, 2025

(54) NANO COMPLEX FOR TARGETED REPAIRING OF NEUROVASCULAR LESION, AND PREPARATION AND USE THEREOF

(71) Applicant: SHANGHAI JIAOTONG UNIVERSITY SCHOOL OF MEDICINE, Shanghai (CN)

(72) Inventors: Xiaoling Gao, Shanghai (CN); Qingxiang Song, Shanghai (CN); Qian Zhang, Shanghai (CN); Hongzhuan Chen, Shanghai (CN); Gan Jiang, Shanghai (CN)

(73) Assignee: SHANGHAI JIAOTONG UNIVERSITY SCHOOL OF MEDICINE, Shanghai (CN)

( * ) Notice: Subject to any disclaimer, the term of this patent is extended or adjusted under 35 U.S.C. 154(b) by 92 days.

(21) Appl. No.: 17/774,575

(22) PCT Filed: Nov. 9, 2020

(86) PCT No.: PCT/CN2020/127588
§ 371 (c)(1),
(2) Date: May 5, 2022

(87) PCT Pub. No.: WO2021/089053
PCT Pub. Date: May 14, 2021

(65) Prior Publication Data
US 2024/0287509 A1    Aug. 29, 2024

(30) Foreign Application Priority Data
Nov. 6, 2019   (CN) .......................... 201911075877.6

(51) Int. Cl.
| C12N 15/113 | (2010.01) |
| A61K 47/64  | (2017.01) |
| A61K 47/65  | (2017.01) |
| A61K 47/69  | (2017.01) |
| A61P 25/28  | (2006.01) |

(52) U.S. Cl.
CPC ............ *C12N 15/113* (2013.01); *A61K 47/64* (2017.08); *A61K 47/65* (2017.08); *A61K 47/6911* (2017.08); *A61P 25/28* (2018.01); *C12N 2310/141* (2013.01)

(58) Field of Classification Search
CPC ............ C12N 15/113; C12N 2310/141; A61K 47/6911; A61K 47/65; A61K 47/64; A61P 25/28
See application file for complete search history.

(56) References Cited

U.S. PATENT DOCUMENTS

| 6,156,748 A       | 12/2000 | Panetta et al. |
| 2009/0081293 A1*  | 3/2009  | Murase ................ A61K 9/5153 |
|                   |         | 514/121 |
| 2010/0183711 A1   | 7/2010  | Mullan et al. |
| 2015/0344525 A1   | 12/2015 | Luo et al. |

FOREIGN PATENT DOCUMENTS

| CN | 90103127.5    |   | 6/1990  |            |
| CN | 97180378.1    |   | 10/1997 |            |
| CN | 2007800180820 |   | 3/2007  |            |
| CN | 101883564  A  |   | 11/2010 |            |
| CN | 102766215  A  |   | 11/2012 |            |
| CN | 103910802  A  | * | 7/2014  |            |
| CN | 104138600  A  | * | 11/2014 |            |
| CN | 2015100518782 |   | 1/2015  |            |
| CN | 108404139  A  | * | 8/2018  |            |
| CN | 201811622989.4|   | 12/2018 |            |
| CN | 2019101495339 |   | 2/2019  |            |
| CN | 2019101591660 |   | 3/2019  |            |
| CN | 110124018  A  |   | 8/2019  |            |
| EP | 0409676    A1 |   | 1/1991  |            |
| WO | WO-2008154638 A2 | * | 12/2008 | ............. C07K 14/47 |

OTHER PUBLICATIONS

Machine translation of CN-103910802-A (Year: 2014).*
Machine translation of CN-104138600-A (Year: 2014).*
Machine translation of CN-108404139-A (Year: 2018).*
Arumugam et al.; "S100P-Derived RAGE Antagonistic Peptide Reduces Tumor Growth and Metastasis"; American Association for Cancer Research; Clin Cancer Res; 18(16) Aug. 15, 2012 4356-4364 (Year: 2012).*

(Continued)

*Primary Examiner* — Robert A Wax
*Assistant Examiner* — John W Lippert, III
(74) *Attorney, Agent, or Firm* — Nath, Goldberg & Meyer; Joshua B. Goldberg

(57) ABSTRACT

Nanocomplex for targeted repairing of neurovascular lesion. The nanocomplex comprises a lipid, an apolipoprotein and a targeted peptide, the targeted peptide formed by covalently linking, through a bridge structure, a nanocarrier linking end and a peptide chain targeting RAGE, which specifically binds to cerebrovascular lesion site. Based on AD and the high expression of RAGE in cerebrovascular and brain parenchyma in diabetic encephalopathy, the nanocomplex, as modified by the targeted peptide, can mainly bind, in a targeted manner, to cerebrovascular endothelium by linking the targeted peptide, to repair vascular endothelial cells, promote removal of Aβ plaque near blood vessels, and repair cerebrovascular and neurovascular unit components such as microglial cells, astrocytes and neurons. Ameliorating cognitive impairment is achieved by combined repairing of multiple components and restoring cerebrovascular functions and cerebral blood flow. The nanocomplex has a disease repair effect and can carry drugs, which are delivered to cerebrovascular lesion site.

17 Claims, 17 Drawing Sheets

Specification includes a Sequence Listing.

(56) References Cited

OTHER PUBLICATIONS

Feb. 7, 2021 International Search Report issued in International Patent Application No. PCT/CN2020/127588.
Feb. 7, 2021 Written Opinion of the International Searching Authority issued in International Patent Application No. PCT/CN2020/127588.
Du Huan, et al. "Research progress of Receptor for Advanced Glycation Endproducts in Alzheimer's Disease" Progress in Modern Biomedicine vol. 14 No. 14 May 2014, doi: 10.13241/j.cnki.pmb.2014.14.043.
Arumugam T, et al. "S100P-Derived RAGE Antagonistic Peptide Reduces Tumor Growth and Metastasis" [J]. Clinical Cancer Research, 2012, 18(16):4356-4364 (Aug. 15, 2012). doi:10.1158/1078-0432.CCR-12-0221.
Rojas A, et al. "Inhibition of RAGE Axis Signaling: A Pharmacological Challenge" [J]. Current Drug Targets, 2018, 19 (3) (Mar. 1, 2019) .DOI: 10.2174/1389450119666180820105956.
Wang S , et al. "Construction of Brain-Targeted Nanoreactor System and Intracerebral Drug Delivery"[J]. J Pharm Biomed Sci , 2017, 7 (12). (Dec. 11, 2017) DOI : https://doi.org/10.20936/jpbms/171201.
Toth P, et al. "Functional vascular contributions to cognitive impairment and dementia: mechanisms and consequences of cerebral autoregulatory dysfunction, endothelial impairment, and neurovascular uncoupling in aging." Am J Physiol Heart Circ Physiol 312: H1-H20, 2017. First published Oct. 28, 2016; doi:10.1152/ajpheart.00581.2016.
Costantino Iadecola. "The Neurovascular Unit Coming of Age: A Journey through Neurovascular Coupling in Health and Disease" Neuron 96, Sep. 27, 2017, http://dx.doi.org/10.1016/j.neuron.2017.07.030.
O. A. Skrobot, et al. "Vascular cognitive impairment neuropathology guidelines (VCING): the contribution of cerebrovascular pathology to cognitive impairment" Brain 2016: 139; 2957-2969.
B. Yew and D. A. Nation. "Cerebrovascular resistance: effects on cognitive decline, cortical atrophy, and progression to dementia" Brain 2017: 140; 1987-2001.
Axel Montagne, et al."Brain imaging of neurovascular dysfunction in Alzheimer's disease"Acta Neuropathol. May 2016 ; 131(5): 687-707. doi:10.1007/s00401-016-1570-0.
Jianping Jia, et al."The cost of Alzheimer's disease in China and re-estimation of costs worldwide" Alzheimer's & Dementia 14 (2018) 483-491.https://doi.org/10.1016/j.jalz.2017.12.006.
Y. Iturria-Medina, et al."Early role of vascular dysregulation on late-onset Alzheimer's disease based on multifactorial data-driven analysis" Nature Communications | 7:11934 | DOI: 10.1038/ncomms11934 | www.nature.com/naturecommunications.
Christopher G. Janson "AD and CAA: Independent risk factors for dementia" Science Translational Medicine Dec. 16, 2015 vol. 7, Issue 318 p. 318ec214 DOI: 10.1126/scitranslmed.aad9005.
Rachel E. Bennett, et al."Tau induces blood vessel abnormalities and angiogenesis-related gene expression in P301L transgenic mice and human Alzheimer's disease" Proc Natl Acad Sci U S A. 2018, 115(6): E1289-E1298. www.pnas.org/cgi/doi/10.1073/pnas.1710329115.
Oct. 5, 2023 EESR issued in European Patent Application No. 20885810.0.
Zhang, Zhihong, et al. "HDL-mimicking peptide-lipid nanoparticles with improved tumor targeting." Small 6.3(2010): 430-437.
Jul. 11, 2023 First Office Action issued in Japanese Patent Application No. 2022-526473 with English translation.

\* cited by examiner

NANO COMPLEX FOR TARGETED REPAIRING OF NEUROVASCULAR LESION, AND PREPARATION AND USE THEREOF

This is a National Phase Application filed under 35 U.S.C. 371 as a national stage of PCT/CN2020/127588, filed Nov. 9, 2020, an application claiming the benefit of Chinese Application No. 201911075877.6, filed Nov. 6, 2019, the content of each of which is hereby incorporated by reference in its entirety.

TECHNICAL FIELD

The present disclosure relates to the fields of nano biomedical material technology-nano drug and drug delivery system, in particular to a new nano complex for targeted repairing of a neurovascular lesion and ameliorating of cognitive impairment, a preparation method therefor and the use thereof.

The Sequence Listing submitted in text format (.txt) filed on Oct. 27, 2022, named "39058U New Sequence Listing ST25.txt", (created on Oct. 25, 2022, 4.50 KB), is incorporated herein by reference.

Background

The brain is a complex organ consuming a large amount of energy, but an energy "reservoir" is absent inside. Blood perfusion of brain tissues by cerebral vessels, especially the ultra-high-density brain microvascular network, plays an extremely important role in maintaining the normal physiological function of the brain (see Am J Physiol Heart Circ Physiol. 2017; 312: H1). With the increase of age and extension of the average human lifespan, multifaceted function impairments in cerebral vessels and microcirculation caused by aging play a key role in the pathogenesis of brain aging and senile cognitive dysfunction (see Neuron. 2017; 96:17). In addition, vascular risk factors such as hypertension, hyperlipidemia, diabetes, ApoE4 genotype and atherosclerosis are critical risk factors for cognitive dysfunction. Cerebral vessel-associated cognitive dysfunction includes mild cognitive dysfunction, Alzheimer's Disease (AD), diabetic encephalopathy, cerebral amyloid angiopathy, post-stroke dementia, vascular dementia, mixed dementia, sub-cortical ischemic vascular dementia, multi-infarct dementia, etc. (Brain. 2016; 139: 2957). Cerebrovascular lesions mainly include increased brain microvascular perfusion resistance, decreased cerebral blood flow (see Brain. 2017; 140:1987), impaired function of various transporters on cerebral vessels, increased permeability of blood brain barrier (BBB), etc. It is estimated that more than 80% of dementias are associated with cerebrovascular lesions; more than 45% of dementias are attributed to (or partially attributed to) aging-related brain microvascular lesions, and cerebrovascular dysfunction occurs much earlier than cognitive decline (Acta Neuropathol. 2016; 131: 687). Therefore, regulation of the cerebrovascular function may become an important strategy for dementia treatment.

AD is the most dominant type of dementia characterized by progressive cognitive dysfunction. It is estimated that there are about 9 million AD patients in China (Alzheimer's & Dementia 2018, 14 (4) 483-491), with one new case added every three seconds. Pathological markers of AD include elevated deposition of amyloid-β (Aβ) plaques in brain parenchyma and cerebral vessels, excessive neurofibrillary tangles, gliosis, and neuronal loss. At present, two categories of FDA-approved anti-AD drugs, a cholinesterase inhibitor and an NMDA receptor antagonist, can only regulate or relieve cognitive functions or symptoms for 6 to 12 months, but cannot prevent or significantly delay the deterioration of this disease. In the past decade, single target-based drugs, such as a γ-secretase inhibitor, a β-secretase inhibitor and an antibody drug mediating Aβ removal, have all failed in a Phase III clinical trial. It can be seen that AD process is complex, which is difficult to be affected by the above-mentioned classical drugs developed on the basis of single target. Therefore, a new-perspective, new-target or multi-target combined treatment strategy will become one of the most promising research directions for AD prevention and treatment.

Previous AD studies have mainly focused on Aβ, Tau protein and neuronal damage, while have long neglected the cerebrovascular function providing important support for brain activity and the significant impact of cerebrovascular lesions on cognitive function. A multifactorial data-driven analysis over brain images, brain samples and the like from 7700 AD patients shows that the loss of cerebrovascular regulatory functions and the high abnormality of vascular function integrity regulatory proteins are observed in the prodromal stage of AD, at which stage mild cognitive impairment (MCI), the earliest lesion in the disease process, occurs (see Nature Communication 2016, 7:11934), even earlier than the deposition of Aβ plaques; and the cerebrovascular abnormality worsens with the progress of the disease. Moreover, in AD, more than 90% of patients have a large number of Aβ plaque depositions in the vascular and peri-vascular regions of the brain. The decrease of cerebral blood flow is closely related to the clinical progress of AD. Cerebral amyloid angiopathy is widespread in the brain of AD patients (see Science Translational Medicine. 2015, 318 (8): 214e-318e), and hyperphosphorylated tau can also damage vascular endothelial cells and destroy vascular integrity (Proc Natl Acad Sci U.S.A. 2018, 115 (6): E1289-E1298). As AD progresses, the multiple connections between nerves and blood vessels (i.e., the structure and function of the neurovascular unit) are constantly damaged, resulting in the constant worsening of cognitive functions. It can be seen therefrom that the cerebrovascular lesion occurs in the early stage of AD, which is particularly important and increasingly recognized for its contribution to the pathogenesis of AD. However, there is currently a lack of an AD intervention strategy for targeted repairing of the neurovascular unit function and then ameliorating of cognitive impairment.

The structure of the neurovascular unit mainly comprises: neurons, vascular smooth muscle cells, vascular endothelial cells, pericytes, astrocytes, microglial cells, oligodendrocytes, and the acellular component—basement membrane. The cerebral neurovascular abnormalities in AD patients can be summarized into the following six aspects: 1) overall decrease in the density of small blood vessels in brain tissues, accompanied by an increase in blood vessel fragments and morphological changes such as vascular atrophy, vascular distortion, and basement membrane thickening; 2) persistent chronic ischemic hypoperfusion: persistent decrease of cerebral blood flow is closely related to the severity of cognitive impairment, which relationship is embodied in that chronic hypoperfusion reduces oxygen, glucose and other nutrients transported to the brain, thereby damaging brain parenchyma, neurovascular units and BBB; the damaged BBB once again leads to insufficient supply of nutrients in the brain, decreased transport of metabolic wastes to the periphery, and difficulty in maintaining cerebral homeostasis; 3) mediation of indirect neurotoxic effects by the damaged BBB by means of promoting oxidative stress, inflammation, affecting glucose transport, etc., thereby forming a vicious circle and aggravating a disease; 4) changes in tight junction, increased transport of peripheral neurotoxic substances to the brain, and lesions of pericyte cell structure; 5) lesions of cells in the brain: abnormal activation of microglial cells, abnormal expression of intracellular proteins in astrocytes, dissociation of astrocytes endfeet from vascular endothelial cells, shrinkage of neuronal cell bodies, axonal thinning and loss of synapses; 6) changes in receptor expression: the expressions of low-density nano complex receptor-related protein 1 (LRP1) and P-glycoprotein (Pgp) on cerebrovascular endothelial cells are down-regulated, while the expression of the receptor for advanced glycation endproducts (RAGE) is up-regulated, and the expression level of RAGE is positively correlated with the severity of AD. The strategy for targeted repairing of the neurovascular units needs to intervene or block multiple targets in the above-mentioned six types of abnormalities, which may be more effective in blocking AD progression and thus treating AD. The abnormally high expression of RAGE can be used as one of the targets of vascular lesions.

The existing disclosed AD treatment strategies mainly focus on single targets such as Aβ and Tau protein, which are poor in clinical efficacy. For example, the published patent CN 200880118761 is mainly targeted at amyloid cerebrovascular lesions; the published patent CN 97180378.1 discloses that the treatment is mainly used for neuroprotection; and the granted patent CN 90103127.5 discloses a cholinesterase inhibitor.

The disclosed nanostructure for AD intervention is mainly used as a drug delivery system, although the nanostructure itself has no drug efficacy: for example, patent CN 201811622989.4 provides an ultra-small nanostructure for drug delivery across the blood brain barrier; for example, patent CN 201910159166.0 provides a nanostructure for delivering a Tau antibody to reduce hyperphosphorylated Tau in the brain. The nanostructure, which is used for drug delivery but itself has no drug efficacy, will bring greater burden to the diseased brain waste removal system in AD, which is not conducive to disease recovery. In addition, there are some single-target nanostructures, for example, patent CN 201910149533.9 discloses delivery of nano-selenium to inhibit hyperphosphorylation of Tau; however, the therapeutic effect of a single target is poor.

Targeting diseased cerebral vessels may provide a new strategy for AD intervention. For example, patent CN 200780018082.0 provides a RAGE antibody, which only acts on the single target RAGE; patent 201510051878.2 provides a specific antagonist peptide (Ala-Pro-Asp-Thr-Lys-Thr-Gln) of RAGE, which can block the transport of AR to the brain by RAGE, but has relatively simple functions, that is, other cells and components in the diseased neurovascular unit cannot be repaired, and therefore, it is difficult to achieve multiple repair effects.

Content of the Present Invention

The first objective of the present disclosure is to provide a nano complex for targeted repairing of a neurovascular lesion, which can effectively treat, in a targeted manner, diseased cerebral vessels mainly by RAGE in the cerebrovascular lesion site, provide a new RAGE targeted peptide-modified nano complex, and relate to a neurovascular unit, so as to repair, in various facets, individual cellular components of the diseased neurovascular unit and ultimately ameliorate cognitive impairment.

The second objective of the present disclosure is to provide a method for preparing the nano complex for targeted repairing of the neurovascular lesion.

The third objective of the present disclosure is to provide use of the nano complex for targeted repairing of the neurovascular lesion in the preparation of a drug for preventing or treating cognitive impairment.

The fourth objective of the present disclosure is to provide use of the nano complex for targeted repairing of the neurovascular lesion in the preparation of a cerebrovascular lesion-targeted drug delivery system with drug-loaded.

The fifth objective of the present disclosure is to provide a targeted peptide for modifying the nano complex for targeted repairing of the neurovascular lesion.

The sixth objective of the present disclosure is to provide use of the targeted peptide for modifying the nano complex for targeted repairing of the neurovascular lesion in the preparation of a cerebrovascular lesion-targeted drug delivery system with drug-loaded.

The seventh objective of the present disclosure is to provide use of the targeted peptide for modifying the nano complex for targeted repairing of the neurovascular lesion in the preparation of a drug for preventing or treating cognitive impairment.

In order to achieve the above-mentioned first objective, the present disclosure provides a nano complex for targeted repairing of a neurovascular lesion, which is characterized in that the nano complex comprises a lipid, an apolipoprotein and a targeted peptide, and the targeted peptide is formed by covalently linking, by means of a bridge structure, a nano-carrier linking end and a peptide chain which targets RAGE, which specifically binds to a cerebrovascular lesion site, wherein the bridge structure comprises: one or more of Gly-Gly (R1), Gly-Ala, Ala-Ala, Ile-Ala (R2), Ile-Gly (R3), Gly-Gly-Gly, Gly-Ser-Gly (R4), Ala-Gly-Ala, Ala-Ser-Ala, Ala-Ala-Ala, Gly-Gly-Ser, Ile-Ala-Ile (R5), Ile-Ser-Ile, Ile-Ile-Ile, Ala-Ala-Ala-Ala, Ala-Leu-Ala-Gly, Gly-Ala-Gly-Ala (R6), Pro-Leu-Gly-Leu, Gly-Gly-Ser-Gly-Gly (R7), Ala-Ala-Ser-Ala-Ala, Gly-Ala-Ser-Ala-Gly, Gly-Ser-Ser-Ser-Gly, Pro-Ala-Ile-Ser-Pro, Gly-Ser-Ser-Ser-Gly-Gly (R8), Pro-Ile-Gly-Leu-Trp-Ala, Gly-Val-Leu-Ala-Glu-Ala and polyethylene glycol.

As a preferred embodiment, the targeted peptide comprises:
AC-Phe-Ala-Glu-Lys-Phe-Lys-Glu-Ala-Val-Lys-Asp-Tyr-Phe-Ala-Lys-Phe-Trp-Asp-Gly-Ser-Gly-Glu-Leu-Lys-Val-Leu-Met-Glu-Lys-Glu-Leu (R4, SEQ ID NO. 1),
AC-Phe-Ala-Glu-Lys-Phe-Lys-Glu-Ala-Val-Lys-Asp-Tyr-Phe-Ala-Lys-Phe-Trp-Asp-Gly-Gly-Glu-Leu-Lys-Val-Leu-Met-Glu-Lys-Glu-Leu (R1, SEQ ID NO. 2),
AC-Phe-Ala-Glu-Lys-Phe-Lys-Glu-Ala-Val-Lys-Asp-Tyr-Phe-Ala-Lys-Phe-Trp-Asp-Ile-Ala-Glu-Leu-Lys-Val-Leu-Met-Glu-Lys-Glu-Leu (R2, SEQ ID NO. 3),
AC-Phe-Ala-Glu-Lys-Phe-Lys-Glu-Ala-Val-Lys-Asp-Tyr-Phe-Ala-Lys-Phe-Trp-Asp-Ile-Gly-Glu-Leu-Lys-Val-Leu-Met-Glu-Lys-Glu-Leu (R3, SEQ ID NO. 4),
AC-Phe-Ala-Glu-Lys-Phe-Lys-Glu-Ala-Val-Lys-Asp-Tyr-Phe-Ala-Lys-Phe-Trp-Asp-Ile-Ala-Ile-Glu-Leu-Lys-Val-Leu-Met-Glu-Lys-Glu-Leu (R5, SEQ ID NO. 5),
AC-Phe-Ala-Glu-Lys-Phe-Lys-Glu-Ala-Val-Lys-Asp-Tyr-Phe-Ala-Lys-Phe-Trp-Asp-Gly-Ala-Gly-Ala-Glu-Leu-Lys-Val-Leu-Met-Glu-Lys-Glu-Leu (R6, SEQ ID NO. 6), AC-Phe-Ala-Glu-Lys-Phe-Lys-Glu-Ala-Val-Lys-Asp-Tyr-Phe-Ala-Lys-Phe-Trp-Asp-Gly-Gly-Ser-Gly-Gly-Glu-Leu-Lys-Val-Leu-Met-Glu-Lys-Glu-Leu (R7, SEQ ID NO. 7), and AC-Phe-Ala-Glu-Lys-Phe-Lys-Glu-Ala-Val-Lys-Asp-Tyr-Phe-Ala-Lys-Phe-Trp-Asp-Gly-Ser-Ser-Ser-Gly-Gly-Glu-Leu-Lys-Val-Leu-Met-Glu-Lys-Glu-Leu (R8, SEQ ID NO. 8), wherein the preferred ones are:

AC-Phe-Ala-Glu-Lys-Phe-Lys-Glu-Ala-Val-Lys-Asp-Tyr-Phe-Ala-Lys-Phe-Trp-Asp-Gly-Ser-Gly-Glu-Leu-Lys-Val-Leu-Met-Glu-Lys-Glu-Leu (R4, SEQ ID NO. 1),

AC-Phe-Ala-Glu-Lys-Phe-Lys-Glu-Ala-Val-Lys-Asp-Tyr-Phe-Ala-Lys-Phe-Trp-Asp-Gly-Gly-Glu-Leu-Lys-Val-Leu-Met-Glu-Lys-Glu-Leu (R1, SEQ ID NO. 2),

AC-Phe-Ala-Glu-Lys-Phe-Lys-Glu-Ala-Val-Lys-Asp-Tyr-Phe-Ala-Lys-Phe-Trp-Asp-Ile-Ala-Ile-Glu-Leu-Lys-Val-Leu-Met-Glu-Lys-Glu-Leu (R5, SEQ ID NO. 5), and AC-Phe-Ala-Glu-Lys-Phe-Lys-Glu-Ala-Val-Lys-Asp-Tyr-Phe-Ala-Lys-Phe-Trp-Asp-Gly-Ala-Gly-Ala-Glu-Leu-Lys-Val-Leu-Met-Glu-Lys-Glu-Leu (R6, SEQ ID NO. 6).

As a preferred embodiment, the lipid is one or more of lecithin, soybean phospholipid, phosphatidylcholine, phosphatidylserine, phosphatidylglycerol, phosphatidic acid, cardiolipin, ceramide, cerebroside, ganglioside, glyceride and a derivative thereof.

As a preferred embodiment, the lipid is monosialotetrahexosyl ganglioside.

As a preferred embodiment, the molar ratio of the targeted peptide to the lipid is 1:10 to 1:500, preferably 1:30.

As a preferred embodiment, the apolipoprotein is one or more of ApoE, ApoA-I, ApoA-II and ApoC-I.

In order to achieve the above-mentioned second objective, the present disclosure provides a method for preparing the nano complex for targeted repairing of the neurovascular lesion, which is characterized in that the method comprises the following steps:

a) synthesizing the above-mentioned targeted peptide by using a solid-phase peptide synthesis method;

b) preparing a lipid by using a conventional method, including a film hydration method, an extrusion method and a continuous flow chip method;

c) firstly adding the targeted peptide to the lipid prepared in b), and then adding an apolipoprotein thereto, wherein the molar ratio of the targeted peptide to the lipid is 1: 10 to 1:500, preferably 1:30, to prepare a targeted peptide-modified nano complex.

In order to achieve the above-mentioned third objective, the present disclosure provides use of the nano complex for targeted repairing of the neurovascular lesion in the preparation of a drug for preventing or treating cognitive impairment.

As a preferred embodiment, the cognitive impairment is Alzheimer's disease and diabetic encephalopathy.

In order to achieve the above-mentioned fourth objective, the present disclosure provides use of the nano complex for targeted repairing of the neurovascular lesion in the preparation of a cerebrovascular lesion-targeted drug delivery system with drug-loaded.

The cerebrovascular lesion-targeted drug delivery system with drug-loaded means that the drug delivery system can carry a drug and deliver the drug to a cerebrovascular lesion site to achieve repairing of the cerebrovascular lesion, in which the nano complex is used as a drug delivery carrier to deliver the drug.

As a preferred embodiment, the drug carried is preferably a drug for preventing or treating cognitive impairment, and the cognitive impairment is preferably Alzheimer's disease and diabetic encephalopathy.

In order to achieve the above-mentioned fifth objective, the present disclosure provides a targeted peptide for modifying the nano complex for targeted repairing of the neurovascular lesion, which is characterized in that the targeted peptide has a sequence as shown in any one of AC-Phe-Ala-Glu-Lys-Phe-Lys-Glu-Ala-Val-Lys-Asp-Tyr-Phe-Ala-Lys-Phe-Trp-Asp-Gly-Ser-Gly-Glu-Leu-Lys-Val-Leu-Met-Glu-Lys-Glu-Leu, AC-Phe-Ala-Glu-Lys-Phe-Lys-Glu-Ala-Val-Lys-Asp-Tyr-Phe-Ala-Lys-Phe-Trp-Asp-Gly-Gly-Glu-Leu-Lys-Val-Leu-Met-Glu-Lys-Glu-Leu, AC-Phe-Ala-Glu-Lys-Phe-Lys-Glu-Ala-Val-Lys-Asp-Tyr-Phe-Ala-Lys-Phe-Trp-Asp-Ile-Ala-Ile-Glu-Leu-Lys-Val-Leu-Met-Glu-Lys-Glu-Leu, or AC-Phe-Ala-Glu-Lys-Phe-Lys-Glu-Ala-Val-Lys-Asp-Tyr-Phe-Ala-Lys-Phe-Trp-Asp-Gly-Ala-Gly-Ala-Glu-Leu-Lys-Val-Leu-Met-Glu-Lys-Glu-Leu, and the nano complex further comprises a lipid and an apolipoprotein.

In order to achieve the above-mentioned sixth objective, the present disclosure provides use of the targeted peptide for modifying the nano complex for targeted repairing of the neurovascular lesion in the preparation of a cerebrovascular lesion-targeted drug delivery system with drug-loaded.

As a preferred embodiment, the drug carried is preferably a drug for preventing or treating cognitive impairment, and the cognitive impairment is preferably Alzheimer's disease and diabetic encephalopathy.

In order to achieve the above-mentioned seventh objective, the present disclosure provides use of the targeted peptide for modifying the nano complex for targeted repairing of the neurovascular lesion in the preparation of a drug for preventing or treating cognitive impairment.

As a preferred embodiment, the cognitive impairment is Alzheimer's disease and diabetic encephalopathy.

The present disclosure has the following advantages: on the basis of the high expression of RAGE in cerebral vessels and brain parenchyma in AD and diabetic encephalopathy, the nano complex, which has been modified by the targeted peptide, is capable of mainly binding, in a targeted manner, to the cerebrovascular endothelium by means of linking the targeted peptide, so as to repair vascular endothelial cells, promote the removal of Aβ plaque near blood vessels, and repair cerebrovascular and neurovascular unit components such as microglial cells, astrocytes and neurons. The aim of ameliorating cognitive impairment is achieved by the combined repairing of multiple components and then restoring cerebrovascular functions and cerebral blood flow. The nano complex itself has a disease repair effect and can also carry drugs, thereby achieving the delivery of drugs to cerebrovascular lesion site.

Detailed Description of the Preferred Embodiment

Figure 1:
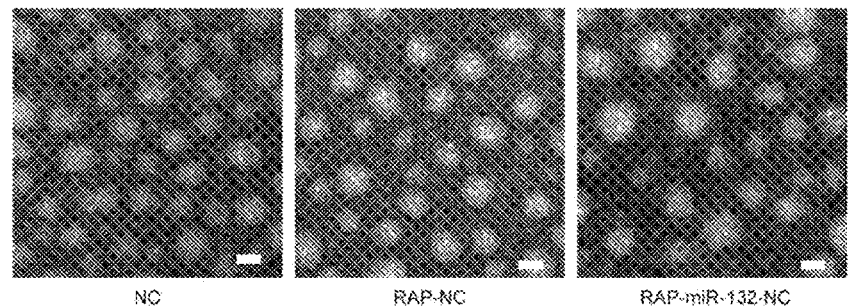
FIG. 1 shows morphologies of a nano complex without a targeted peptide, a targeted peptide-containing nano complex, and a targeted peptide-containing nano complex with a microRNA-132 drug-loaded, as observed by a transmission electron microscope (Scale bar: 20 nm).

The present techniques are described below in detail in conjunction with specific examples. It should be understood that the following specific examples are provided only for aiding the understanding of the present disclosure by those skilled in the art, but are not construed as limiting the present disclosure.

Example 1. Preparation and Characterization of a Targeted Peptide-Containing Nano Complex (1) Preparation Preparation of an ordinary liposome by using a film hydration method: lipids (soybean phospholipid, lecithin phosphatidylcholine or ganglioside) were weighed and placed in a round-bottom flask; 2 to 8 mL of chloroform was added thereto; and the mixture was placed on a rotary evaporator and evacuated for 1 h. To the mixture was added 4 to 16 mL of 0.01 M PBS solution (pH 7.4), and shaken for 10 min until the film hydrates and sheds to obtain a liposome. In a water bath at 37° C., the particle diameter of the liposome was reduced by an ultrasound probe to obtain an ordinary liposome.

A targeted peptide was synthesized by using a solid-phase polypeptide synthesis method.

The bridge structure was one or more of Gly-Gly (R1), Gly-Ala, Ala-Ala, Ile-Ala (R2), Ile-Gly (R3), Gly-Gly-Gly, Gly-Ser-Gly (R4), Ala-Gly-Ala, Ala-Ser-Ala, Ala-Ala-Ala, Gly-Gly-Ser, Ile-Ala-Ile (R5), Ile-Ser-Ile, Ile-Ile-Ile, Ala-Ala-Ala-Ala, Ala-Leu-Ala-Gly, Gly-Ala-Gly-Ala (R6), Pro-Leu-Gly-Leu, Gly-Gly-Ser-Gly-Gly (R7), Ala-Ala-Ser-Ala-Ala, Gly-Ala-Ser-Ala-Gly, Gly-Ser-Ser-Ser-Gly, Pro-Ala-Ile-Ser-Pro, Gly-Ser-Ser-Ser-Gly-Gly (R8), Pro-Ile-Gly-Leu-Trp-Ala, Gly-Val-Leu-Ala-Glu-Ala and polyethylene glycol.

For example, α-RAP comprised AC-Phe-Ala-Glu-Lys-Phe-Lys-Glu-Ala-Val-Lys-Asp-Tyr-Phe-Ala-Lys-Phe-Trp-Asp-Gly-Ser-Gly-Glu-Leu-Lys-Val-Leu-Met-Glu-Lys-Glu-Leu (R4, SEQ ID NO. 1), AC-Phe-Ala-Glu-Lys-Phe-Lys-Glu-Ala-Val-Lys-Asp-Tyr-Phe-Ala-Lys-Phe-Trp-Asp-Gly-Gly-Glu-Leu-Lys-Val-Leu-Met-Glu-Lys-Glu-Leu (R1, SEQ ID NO. 2), AC-Phe-Ala-Glu-Lys-Phe-Lys-Glu-Ala-Val-Lys-Asp-Tyr-Phe-Ala-Lys-Phe-Trp-Asp-Ile-Ala-Glu-Leu-Lys-Val-Leu-Met-Glu-Lys-Glu-Leu (R2, SEQ ID NO. 3), AC-Phe-Ala-Glu-Lys-Phe-Lys-Glu-Ala-Val-Lys-Asp-Tyr-Phe-Ala-Lys-Phe-Trp-Asp-Ile-Gly-Glu-Leu-Lys-Val-Leu-Met-Glu-Lys-Glu-Leu (R3, SEQ ID NO. 4), AC-Phe-Ala-Glu-Lys-Phe-Lys-Glu-Ala-Val-Lys-Asp-Tyr-Phe-Ala-Lys-Phe-Trp-Asp-Ile-Ala-Ile-Glu-Leu-Lys-Val-Leu-Met-Glu-Lys-Glu-Leu (R5, SEQ ID NO. 5), AC-Phe-Ala-Glu-Lys-Phe-Lys-Glu-Ala-Val-Lys-Asp-Tyr-Phe-Ala-Lys-Phe-Trp-Asp-Gly-Ala-Gly-Ala-Glu-Leu-Lys-Val-Leu-Met-Glu-Lys-Glu-Leu (R6, SEQ ID NO. 6), AC-Phe-Ala-Glu-Lys-Phe-Lys-Glu-Ala-Val-Lys-Asp-Tyr-Phe-Ala-Lys-Phe-Trp-Asp-Gly-Gly-Ser-Gly-Gly-Glu-Leu-Lys-Val-Leu-Met-Glu-Lys-Glu-Leu (R7, SEQ ID NO. 7), and AC-Phe-Ala-Glu-Lys-Phe-Lys-Glu-Ala-Val-Lys-Asp-Tyr-Phe-Ala-Lys-Phe-Trp-Asp-Gly-Ser-Ser-Ser-Gly-Gly-Glu-Leu-Lys-Val-Leu-Met-Glu-Lys-Glu-Leu (R8, SEQ ID NO. 8).

The specific method was as follows: amino acids were linked to a chloromethyl polystyrene resin, and an amino protecting group was removed under the protection of trifluoroacetic acid. Then the amino acids were cleaved by hydrogen fluoride, precipitated in an ether ice bath, dissolved in acetonitrile, and then subjected to rotary evaporation, and further purified by an acetonitrile-water system.

To a liposome solution was added 1 part of the targeted peptide, placed on a shaker, and incubated at 120 rpm, 37° C. for 36 h to obtain a targeted peptide-containing liposome, wherein the parts were all parts by molar ratio.

To the above-mentioned targeted peptide-containing liposome was added 0.06 to 0.6 parts (molar ratio) of ApoE or ApoA-I, mixed homogeneously and gently, placed on a shaker, and incubated at 120 rpm, 37° C. for 36 h to obtain a targeted peptide-modified nano complex (i.e., RAP peptide modifying nano complex, abbreviated as RAP-NC).

(2) Characterization

Figure 2A:
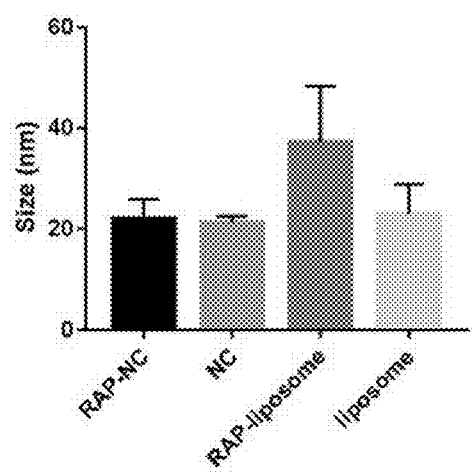
FIG. 2 shows the particle diameter (size), polymer dispersity index (PDI) and surface potential (zeta potential) of a targeted peptide-modified nano complex.
Figure 2B:
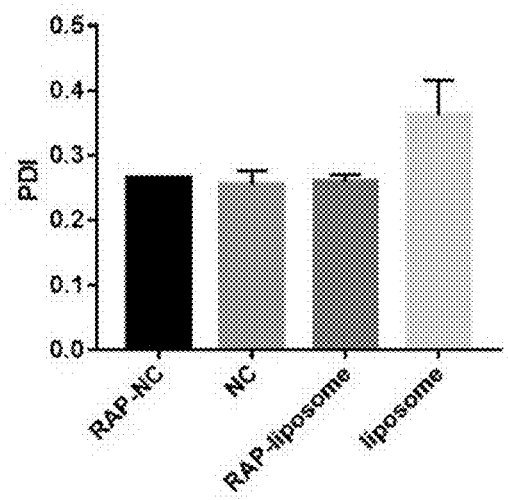
Figure 2C:
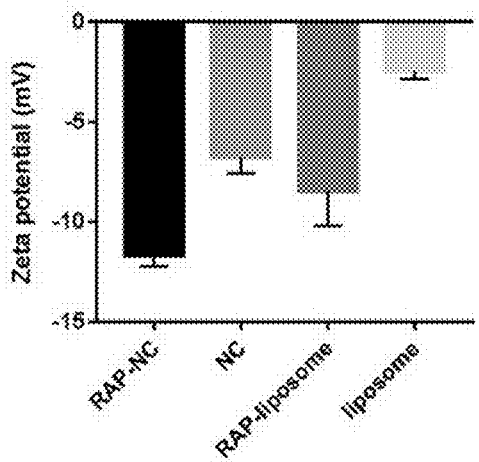

The targeted peptide-modified nano complex was negatively stained with a phosphotungstic acid solution, and was observed for the morphology thereof by a transmission electron microscope. As shown in FIG. 1, under the electron microscope, the targeted peptide-modified nano complex was in a uniform spherical shape, with a uniform dispersion and a particle diameter of 20 to 30 nm. The liposome was determined for the particle diameter and surface potential thereof by a laser particle analyzer (as shown in FIG. 2). Compared with the ordinary liposome, the targeted peptide-containing liposome has reduced polymer dispersity index (PDI), more uniform particle diameter, and reduced surface potential. After ApoE was co-incubated, the targeted peptide-containing nano complex was determined for having a particle diameter of about 20 to 30 nm and a more negative surface potential. Combined with the above-mentioned electron microscope results, it showed that the negatively charged ApoE protein was successfully self-assembled with the targeted peptide-containing liposome to form a targeted peptide-containing nano complex, which has a special nanostructure of 20 to 30 nanometers in size.

Example 2. Screening of a bridge structure peptide segment for linking a nanocarrier linking end and a peptide chain which targets diseased blood vessels (1) Preparation A variety of targeted peptides containing a bridge structure peptide segment for linking a nanocarrier linking end and a peptide chain which targets diseased blood vessels were synthesized by using a solid-phase polypeptide synthesis method as described in Example 1, except of substitution of bridge structures in Example 1 with the following polypeptides: Gly-Gly (R1), Ile-Ala (R2), Ile-Gly (R3), Gly-Gly-Gly, Gly-Ser-Gly (R4), Ile-Ala-Ile (R5), Gly-Ala-Gly-Ala (R6), Gly-Gly-Ser-Gly-Gly (R7), and Gly-Ser-Ser-Ser-Gly-Gly (R8). The following targeted peptides was obtained accordingly:

AC-Phe-Ala-Glu-Lys-Phe-Lys-Glu-Ala-Val-Lys-Asp-Tyr-Phe-Ala-Lys-Phe-Trp-Asp-Gly-Ser-Gly-Glu-Leu-Lys-Val-Leu-Met-Glu-Lys-Glu-Leu (R4, SEQ ID NO. 1),

AC-Phe-Ala-Glu-Lys-Phe-Lys-Glu-Ala-Val-Lys-Asp-Tyr-Phe-Ala-Lys-Phe-Trp-Asp-Gly-Gly-Glu-Leu-Lys-Val-Leu-Met-Glu-Lys-Glu-Leu (R1, SEQ ID NO. 2),

AC-Phe-Ala-Glu-Lys-Phe-Lys-Glu-Ala-Val-Lys-Asp-Tyr-Phe-Ala-Lys-Phe-Trp-Asp-Ile-Ala-Glu-Leu-Lys-Val-Leu-Met-Glu-Lys-Glu-Leu (R2, SEQ ID NO. 3),

AC-Phe-Ala-Glu-Lys-Phe-Lys-Glu-Ala-Val-Lys-Asp-Tyr-Phe-Ala-Lys-Phe-Trp-Asp-Ile-Gly-Glu-Leu-Lys-Val-Leu-Met-Glu-Lys-Glu-Leu (R3, SEQ ID NO. 4),

AC-Phe-Ala-Glu-Lys-Phe-Lys-Glu-Ala-Val-Lys-Asp-Tyr-Phe-Ala-Lys-Phe-Trp-Asp-Ile-Ala-Ile-Glu-Leu-Lys-Val-Leu-Met-Glu-Lys-Glu-Leu (R5, SEQ ID NO. 5),

AC-Phe-Ala-Glu-Lys-Phe-Lys-Glu-Ala-Val-Lys-Asp-Tyr-Phe-Ala-Lys-Phe-Trp-Asp-Gly-Ala-Gly-Ala-Glu-Leu-Lys-Val-Leu-Met-Glu-Lys-Glu-Leu (R6, SEQ ID NO. 6),

AC-Phe-Ala-Glu-Lys-Phe-Lys-Glu-Ala-Val-Lys-Asp-Tyr-Phe-Ala-Lys-Phe-Trp-Asp-Gly-Gly-Ser-Gly-Gly-Glu-Leu-Lys-Val-Leu-Met-Glu-Lys-Glu-Leu (R7, SEQ ID NO. 7), and AC-Phe-Ala-Glu-Lys-Phe-Lys-Glu-Ala-Val-Lys-Asp-Tyr-Phe-Ala-Lys-Phe-Trp-Asp-Gly-Ser-Ser-Ser-Gly-Gly-Glu-Leu-Lys-Val-Leu-Met-Glu-Lys-Glu-Leu (R8, SEQ ID NO. 8).

Targeted peptide-modified nano complexes containing the above-mentioned multiple targeted peptides were prepared as described in Example 1. During preparation, a red fluorescent dye DiI (0.3 to 3 parts by molar ratio) was added to a lipid chloroform solution in a round-bottom flask, with the remaining steps being the same, to prepare a red fluorescence-labeled nano complex modified with multiple targeted peptides.

(2) Comparison of Cellular Uptake

Figure 3:
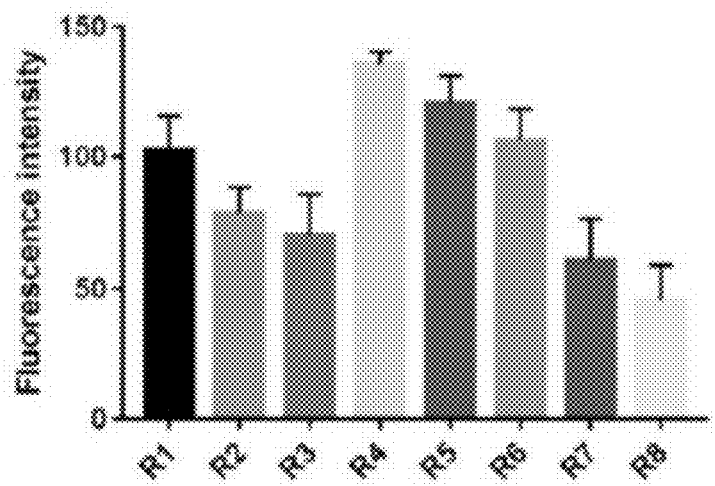
FIG. 3 shows the effect of targeted peptides with different bridge structure peptide segments on uptake of a nano complex by a cerebrovascular endothelial cell line.

High-content quantitative analysis was performed to determine cellular uptake of each of the above-mentioned nano complexes. Mouse-derived cerebrovascular endothelial cells bEnd3 cells were seeded in a 96-well plate at a density of 5000/well and cultured for 24 h. The original culture solution was aspirated and discarded, and 100 μL of the above-mentioned 8 red fluorescence-labeled nanostructure solutions (5 μg/mL, calculated by lipid mass) were added, respectively; the mixture was incubated in a cell incubator for 6 h, then fixed with 3.7% formaldehyde at 37° C. for 10 min, nuclear stained with Hoechst for 10 min, washed three times with PBS, and then photographed and subjected to quantitative analysis with a high-content Target Activation procedure. The results were shown in FIG. 3. Cerebrovascular endothelial cells had a good effect on uptake of nano complexes prepared by the targeted peptides with peptides R1, R2, R3, R4, R5, R6, R7 and R8 as bridge structure peptides. Among them, the cerebrovascular endothelial cells had a better uptake of nano complexes prepared by the targeted peptides with R1, R4, R5 and R6 as bridge structure peptides, and the best uptake of a nano complex prepared by the targeted peptide with peptide R4 (with the bridge structure peptide of Gly-Ser-Gly) as a bridge structure peptide, that is, AC-Phe-Ala-Glu-Lys-Phe-Lys-Glu-Ala-Val-Lys-Asp-Tyr-Phe-Ala-Lys-Phe-Trp-Asp-Gly-Ser-Gly-Glu-Leu-Lys-Val-Leu-Met-Glu-Lys-Glu-Leu (R4, SEQ ID NO. 1) was the optimal targeted peptide.

(3) Comparison of Vascular Binding Capacity

Figure 4:
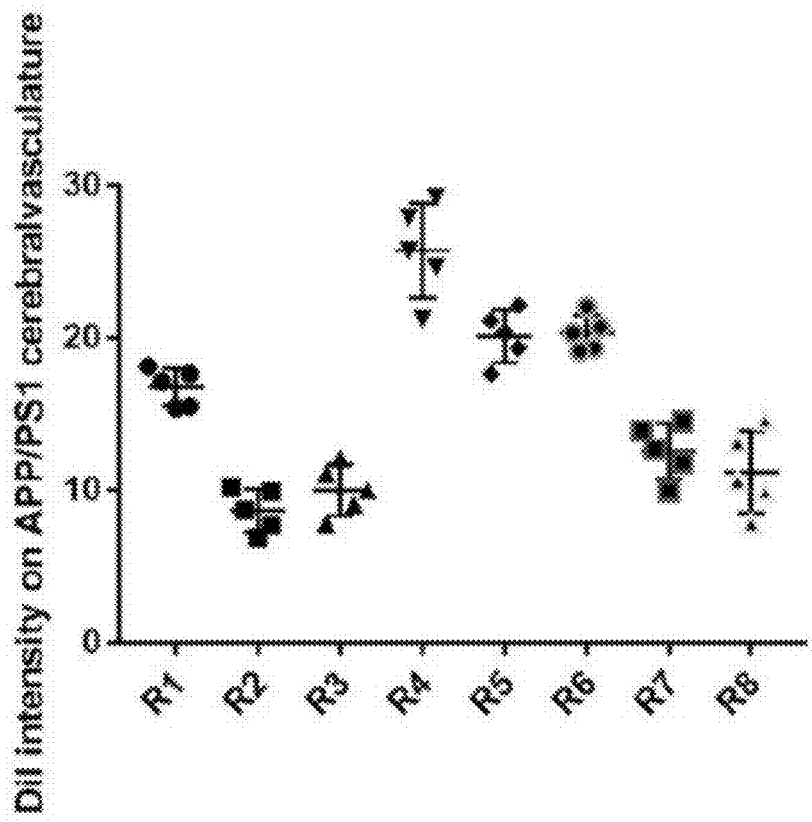
FIG. 4 shows the effect of modification of targeted peptides with different bridge structure peptide segments on binding ability of a nano complex to cerebral vessels of AD model mice.

The AD model animal mice were administered via tail veins with the above-mentioned red fluorescence-labeled nano complexes modified with targeted peptides (containing 8 bridge structure peptides), and were sacrificed 3 hours later. The mice were perfused with normal saline until the blood was not red, and the brain thereof was taken and photographed by a two-photon microscope. The nano complexes bound on cerebral vessels were imaged, and Image J image analysis software was used to analyze the fluorescence intensity of the red fluorescence-labeled nano complexes bound on the cerebral vessels. The results were shown in FIG. 4, and the targeted peptides with R1, R4, R5 and R6 as bridge structure peptides, which modify the nano complexes, were still the dominant targeted peptides, wherein AC-Phe-Ala-Glu-Lys-Phe-Lys-Glu-Ala-Val-Lys-Asp-Tyr-Phe-Ala-Lys-Phe-Trp-Asp-Gly-Ser-Gly-Glu-Leu-Lys-Val-Leu-Met-Glu-Lys-Glu-Leu (R4, SEQ ID NO. 1) was the optimal targeted peptide.

Example 3. Screening for Necessity of Each Component of a Targeted Peptide-Modified Nano Complex and for Addition Order Thereof in the Preparation (1) Preparation Each component of a targeted peptide-modified nano complex is an essential component for specific targeting of cerebrovascular endothelial cells, and the addition order of the targeted peptide in the preparation (with respect to ApoE) affects the ability to target diseased blood vessels. The following substances were prepared as described in the method of Example 2: a red fluorescence-labeled ordinary liposome containing only phosphatidylcholine, a targeted peptide-containing liposome, a ganglioside (GM1)-containing nano complex, a GM1-free targeted peptide-containing nano complex, a nanostructure in which a nano complex was added first for incubation and then a targeted peptide was added, and a targeted peptide-modified nano complex.

(2) Comparison of Cellular Uptake

Figure 5:
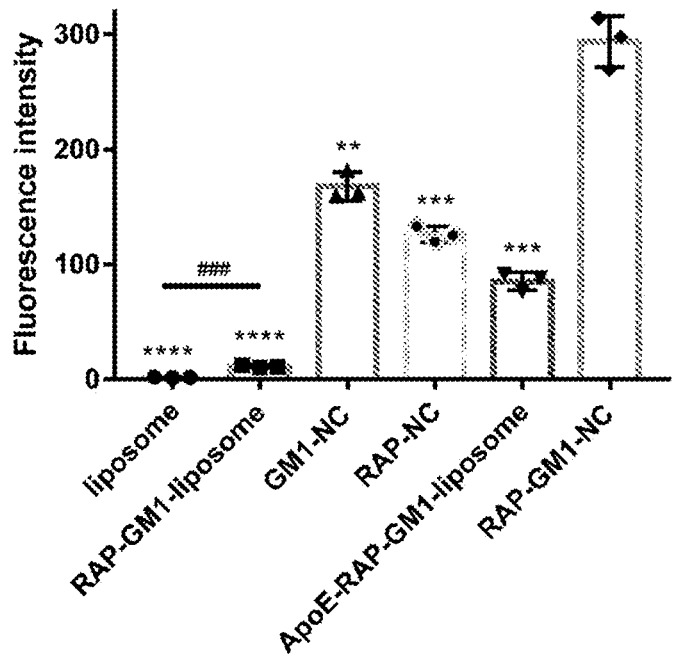
FIG. 5 shows the effect of each component and the addition order of a targeted peptide and a lipoprotein in the preparation on uptake of a targeted peptide-modified fluorescently labeled nano complex with drug-loaded by a cerebrovascular endothelial cell line, wherein  represents $p<0.01$; * represents $p<0.001$; **** represents $p<0.0001$, indicating that there is a significant difference compared with a targeted peptide-modified nano complex; and ### represents $p<0.001$, indicating that there is a significant difference compared with an ordinary liposome (liposome), n=3.

High-content quantitative analysis was performed on cellular uptake of each of the above-mentioned nanostructures. Mouse-derived cerebrovascular endothelial cells were plated, to which the above-mentioned 6 nanostructure solutions were added respectively; the mixture was incubated in a cell incubator for 6 h, then fixed, nuclear stained, and photographed and subjected to high-content quantitative analysis. The results were shown in FIG. 5. The uptake of a targeted peptide-modified liposome by brain capillary endothelial cells was significantly higher than that of an ordinary liposome, indicating that when only a targeted peptide was added, cellular uptake could also be partially promoted. The uptake of a targeted peptide-modified nano complex was the highest, which was 174 times that of an ordinary liposome and was significantly higher than that of a nano complex and a targeted peptide-modified ganglioside-free nano complex, indicating that GM1, a targeted peptide and an apolipoprotein (ApoE or ApoA1) are essential components of the nano complex. In addition, the uptake of a targeted peptide-modified nano complex was also significantly higher than that of a nanostructure in which a lipoprotein was incubated first and then a targeted peptide was incubated (2.9 times), indicating that in preparation, a liposome needed to be incubated with a targeted peptide first, and then incubated with an apolipoprotein, so as to produce the optimal targeting of cerebrovascular endothelial cells.

Figure 6A:
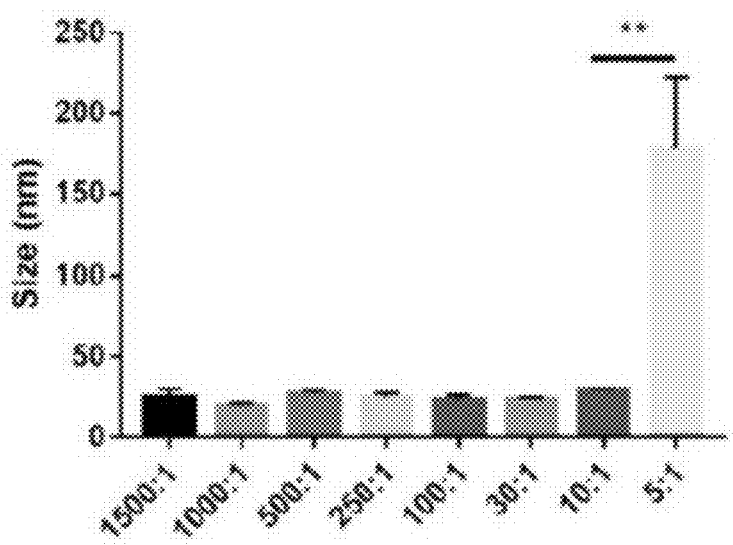
FIG. 6 shows the particle diameter (a), polymer dispersity index (b) and surface potential (c) of nano complexes containing targeted peptides of different molar ratios, n=3.
Figure 6B:
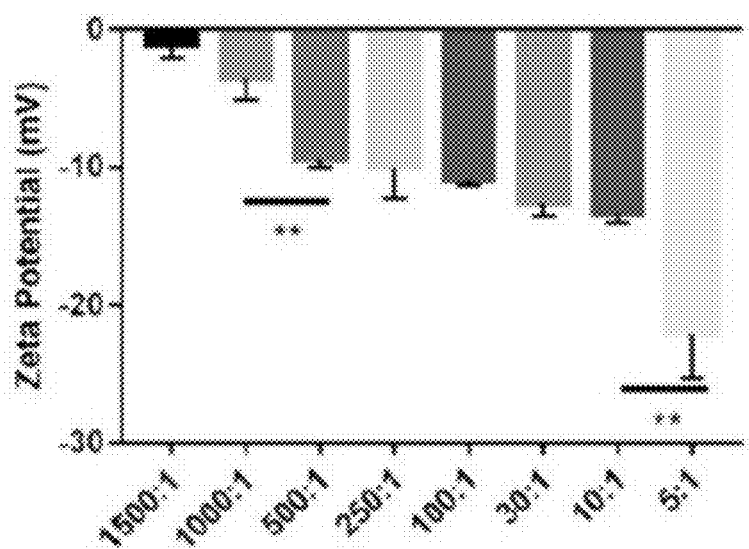
Figure 6C:
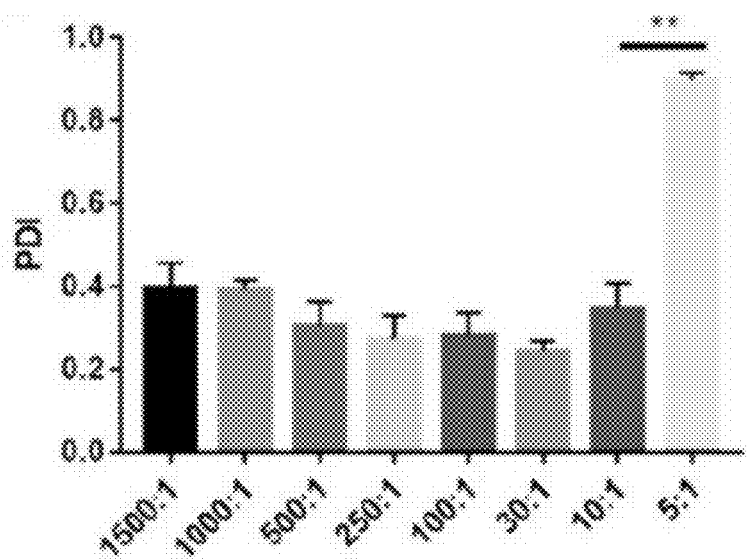
Figure 7:
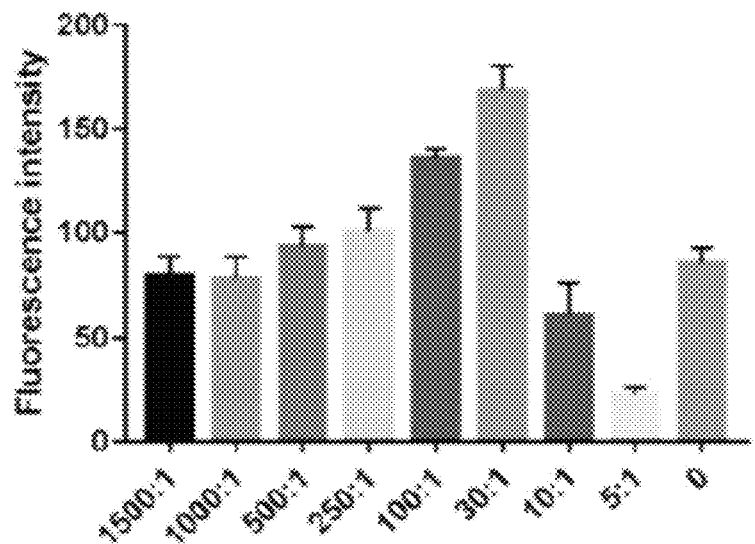
FIG. 7 shows the difference in cellular uptake of a fluorescently labeled nano complex without a targeted peptide and nano complexes modified with targeted peptides of different molar ratios by a cerebrovascular endothelial cell line.

Example 4. Screening for Ratios of Targeted Peptides in Preparation (1) Effect of ratios of targeted peptides on the particle diameter of a nano complex
  The targeted peptide is a ligand that specifically targets diseased blood vessels, the addition ratio of which in the preparation of a targeted peptide-modified nano complex affects the ability to target diseased blood vessels. Targeted peptides of different ratios (1500:1, 1000:1, 500:1, 250:1, 100:1, 30:1, 10:1, and 5:1, the molar ratio of the lipid to the targeted peptide) were added to prepare a targeted peptide-modified nano complex as described in the method of Example 1; as shown in FIG. 6, excessive targeted peptides would result in too large particle diameter, too large PDI, and non-uniform particle diameter of the nano complex. However, targeted peptides of too low ratios would result in insufficient entanglement for the nano complex, with 500:1 to 10:1 being the dominant ratio range, and 30:1 being the dominant ratio among them.
(2) Effect of Ratios of Targeted Peptides on the Ability of Targeting Cerebrovascular Endothelial Cells
  Moreover, a red fluorescence-labeled targeted nano complex was prepared as described in the method of Example 2. Cellular uptake of a targeted peptide-modified nano complex was subjected to high-content quantitative analysis. The cerebrovascular endothelial cells were treated with targeted peptide-modified nano complexes containing targeted peptides of different ratios (1500:1, 1000:1, 500:1, 250:1, 100:1, 30:1, 10:1, and 5:1, the molar ratio of the lipid to the targeted peptide); the mixture was incubated in a cell incubator for 6 h, then fixed, nuclear stained, and subjected to high-content quantitative analysis. The results were shown in FIG. 7. The dominant ratio range was 500:1 to 10:1, and brain capillary endothelial cells had the highest uptake for the targeted peptide (30:1)-modified nano complex. Combined with effect of the ratio on the particle diameter of the nano complex in this example, it was shown that 500:1 to 10:1 was the dominant ratio range, and 30:1 was the dominant ratio of the targeted peptide.

Figure 8:
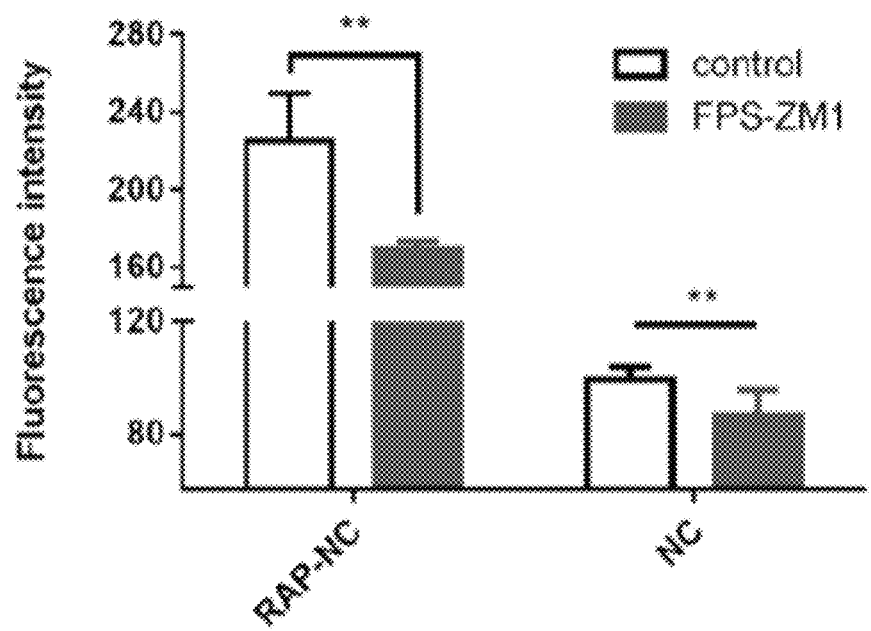
FIG. 8 shows the difference in cellular uptake of a fluorescently labeled nano complex without a targeted peptide and a targeted peptide-modified nano complex by a cerebrovascular endothelial cell line without or with addition of a RAGE inhibitor FPS-ZM1, wherein ** represents $p<0.01$, indicating that there is a significant difference compared with a treatment group without an inhibitor, n=5.

Example 5. Inhibitory Effect of a RAGE Inhibitor on Uptake of a Targeted Peptide-Modified Nano Complex by bEnd.3 Cells 5 μM of RAGE inhibitor, FPS-ZM1 was added to cerebrovascular endothelial cells, with DMEM as a normal control; the mixture was incubated for 1 h, and then a fluorescently labeled nano complex solution and a RAGE targeted peptide-modified nano complex solution were added thereto; the resulting mixture was incubated in a cell incubator for 3 h, then fixed, nuclear stained, and subjected to high-content quantitative analysis, as described in the method of Example 2. The results were shown in FIG. 8, and it was found that a RAGE inhibitor significantly inhibited cellular uptake of a RAGE targeted peptide-modified nano complex, with a 25% ±5% reduction in uptake, indicating that the uptake was partially inhibited. In addition, FPS-ZM1 could not inhibit cellular uptake of a nano complex, indicating that the uptake of a targeted peptide-modified nano complex by cerebrovascular endothelial cells was mediated partially by the RAP-RAGE interaction, that is, the targeted peptide-modified nano complex was uptaken by brain capillary endothelial cells by means of mediation of abnormally high expression of RAGE on cerebral vessels.

Figure 9:
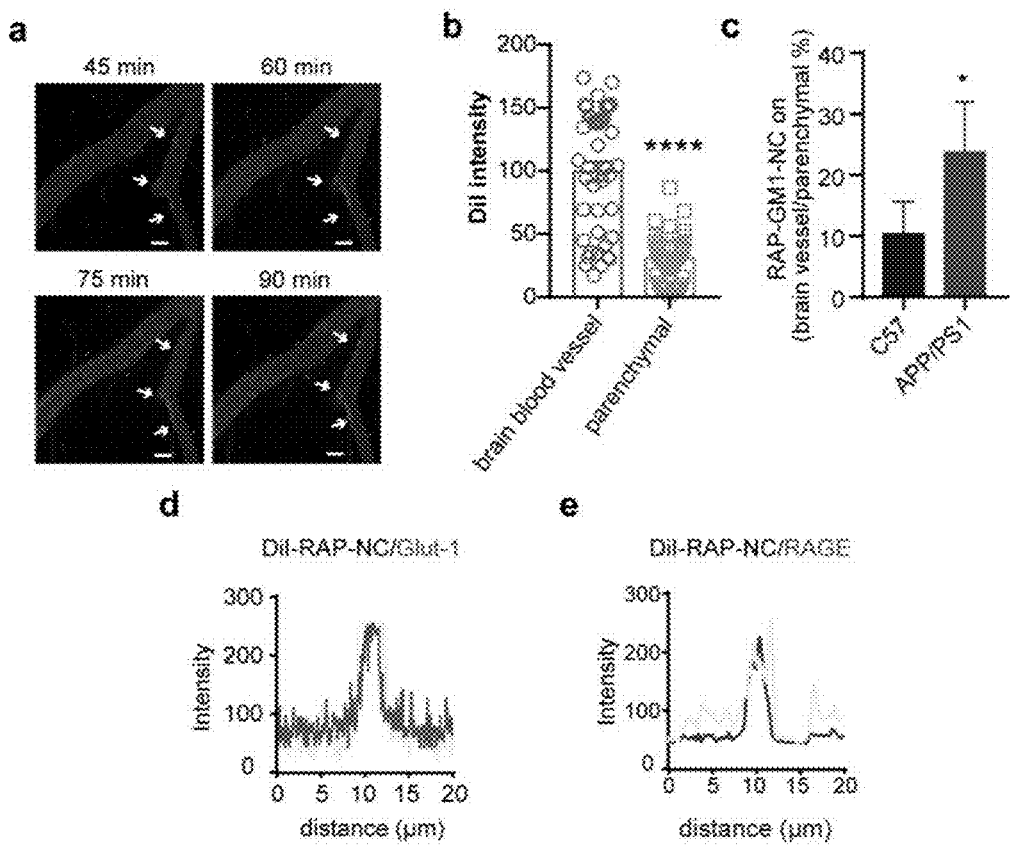
FIG. 9 shows binding of a fluorescently labeled targeted peptide-modified nano complex to diseased cerebral vessels in AD model mice. Panel (a) shows a picture of binding of a targeted peptide-modified nano complex to cerebral vessels, as taken by an in-vivo multiphoton microscope (Scale bar: 20 μm); panel (b) shows distribution difference of a targeted peptide-modified nano complex in cerebral vessels and brain parenchyma, wherein **** represents $p<0.0001$, indicating that there is a significant difference compared with the amount of the nano complex in brain parenchyma; panel (c) shows the difference in binding of a targeted peptide-modified nano complex to cerebral vessels of normal (C57) mice and AD model mice (APP/PS1), wherein * represents $p<0.05$, indicating that there is a significant difference compared with the amount of the nano complex in cerebral vessels and brain parenchyma of normal young C57 mice; panel (d) shows a colocalization profile of a targeted peptide-modified nano complex distributed in cerebral vessels and of glucose transporter 1 (Glut1) on cerebral vessels; panel (e) shows a colocalization profile of a targeted peptide-modified nano complex on cerebral vessels and of RAGE.

Example 6. Specific Binding of a Targeted Peptide-Modified Nano Complex to Diseased Cerebral Vessels in In-Vivo AD Model Animals A red fluorescence-labeled targeted peptide-modified nano complex was prepared as described in Example 1. AD model animal APP/PS1 mice were administered via tail veins with a targeted peptide-modified nano complex (dose: 5 mg/kg by lipids), anesthetized and subjected to craniotomy, and then placed under a multiphoton microscope for real-time monitoring of the accumulation of the targeted peptide-modified nano complex in cerebral vessels. The results showed that the targeted peptide-modified nano complex was mainly accumulated on the inner wall of the cerebral vessels (FIG. 9*a*). 3.5 h after administration, the mice were sacrificed and perfused, and then the brain thereof was taken for being prepared into a frozen section, and cerebral vessels were photographed by a laser confocal microscope and subjected to quantitative analysis. The results showed that the targeted peptide-modified nano complex had a binding amount in the cerebral vessels of the cerebral cortex and the hippocampus region significantly higher than that in the cerebral vessels of the brain parenchyma (FIG. 9*b*). The targeted peptide-modified nano complex had a binding to the cerebral vessels in AD model (APP/PS1) mice significantly higher than that in normal (C57) mice. Cerebrovascular endothelial cells were immunostained with a glucose transporter 1 (GLUT1) antibody, and the results showed that GLUT1 was completely co-localized with a targeted peptide-modified nano complex, confirming that the targeted peptide-modified nano complex indeed specifically bound to the diseased cerebral vessels due to AD (FIG. 9*d*). RAGE on cerebrovascular endothelial cells was immunostained with a RAGE antibody, and the results showed that RAGE was better co-localized with a targeted peptide-modified nano complex, confirming that the targeted peptide-modified nano complex indeed specifically bind to the diseased cerebral vessels due to AD by RAGE (FIG. 9*e*).

Figure 10:
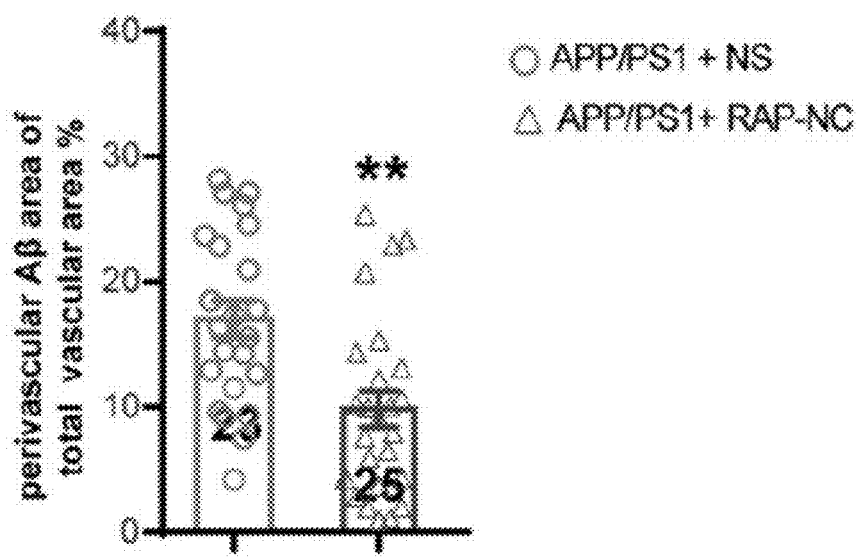
FIG. 10 shows that a targeted peptide-modified nano complex promotes removal of Aβ plaque depositions in the peri-vascular regions of the brain in AD model mice: the figure shows the ratio of the perivascular Aβ plaque area to the corresponding vascular area, wherein the number of samples is calculated as 23 and 25, and ** represents $p<0.01$, indicating that there is a significant difference compared with a normal saline group.

Example 7. Promotion of Removal of Aβ Amyloid Plaques Near Diseased Cerebral Vessels in AD Model Animals by a Targeted Peptide-Modified Nano Complex A red fluorescence-labeled targeted peptide-modified nano complex was prepared as described in Example 1. 13-month-old APP/PS1 mice were administered via tail veins with the nano complex, and after 4 weeks, the mice were administered intraperitoneally with X04 to stain Aβ amyloid plaques, and administered via tail veins with red fluorescence-labeled dextran to label blood vessels, and the Aβ amyloid plaques near the blood vessels were photographed by an in-vivo multiphoton microscope, indicating that the targeted peptide-modified nano complex promotes the removal of the Aβ plaques near the blood vessels, with a reduction of 42% of the Aβ plaques near the blood vessels (FIG. 10).

Figure 11A:
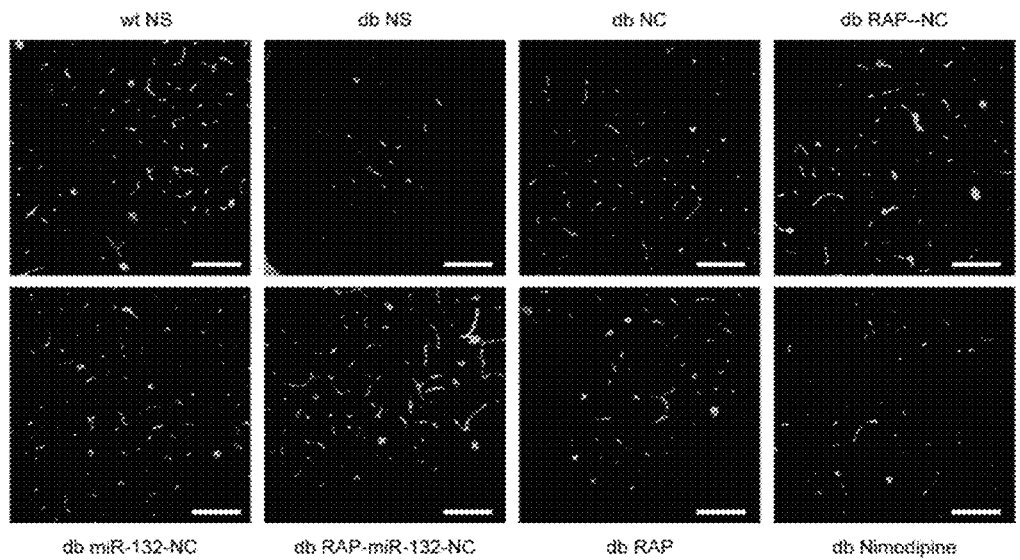
FIG. 11 shows that a targeted peptide-modified nano complex improves the density of diseased cerebral vessels. Panel (a) shows that a targeted peptide-modified nano complex improves the cerebrovascular density of a diabetic encephalopathy model, which is better than that of a targeted peptide, a nano complex and nimodipine alone; a targeted peptide-modified nano complex with miR-132-loaded further improves the cerebrovascular density (Scale bar: 100 μm). Panel (b) shows that a targeted peptide-modified nano complex improves the cerebrovascular morphology and cerebral blood flow in in-vivo AD model mice.

Example 8. Improvement of Cerebrovascular Abnormalities in Diabetic Encephalopathy Model and AD Model Mice and Increase of Cerebrovascular Density by a Targeted Peptide-Modified Nano Complex (1) Diabetic Encephalopathy Model Diabetic encephalopathy model mice db/db mice (db) and littermate wild-type control mice (wild type, wt) were administered via tail veins with a targeted peptide-modified nano complex, and after 2 weeks, the mice were administered via tail veins with green fluorescence-labeled dextran to label blood vessels, and a picture for continuous multi-layered cerebral vessels was taken by an in-vivo multiphoton microscope, which was subjected to three-dimensional reconstruction into a picture showing three-dimensional cerebral vessels, indicating that the targeted peptide-modified nano complex effectively enhanced the cerebrovascular density in db mice (FIG. 11a).

Figure 11B:
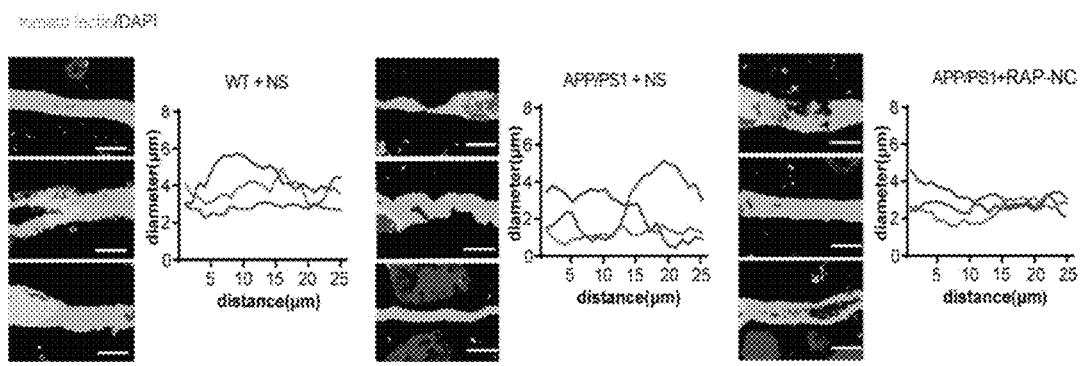

(2) AD Model 10-month-old APP/PS1 mice were administered via tail veins with a targeted peptide-modified nano complex for 4 weeks, then perfused and fixed, and the brain thereof was taken for being prepared into a frozen section, and the cerebral vessels were stained with Tomato lectin for morphology, showing that the targeted peptide-modified nano complex effectively improved the diameter, morphology and smoothness of the cerebral vessels in AD model mice (FIG. 11b).

Figure 12:
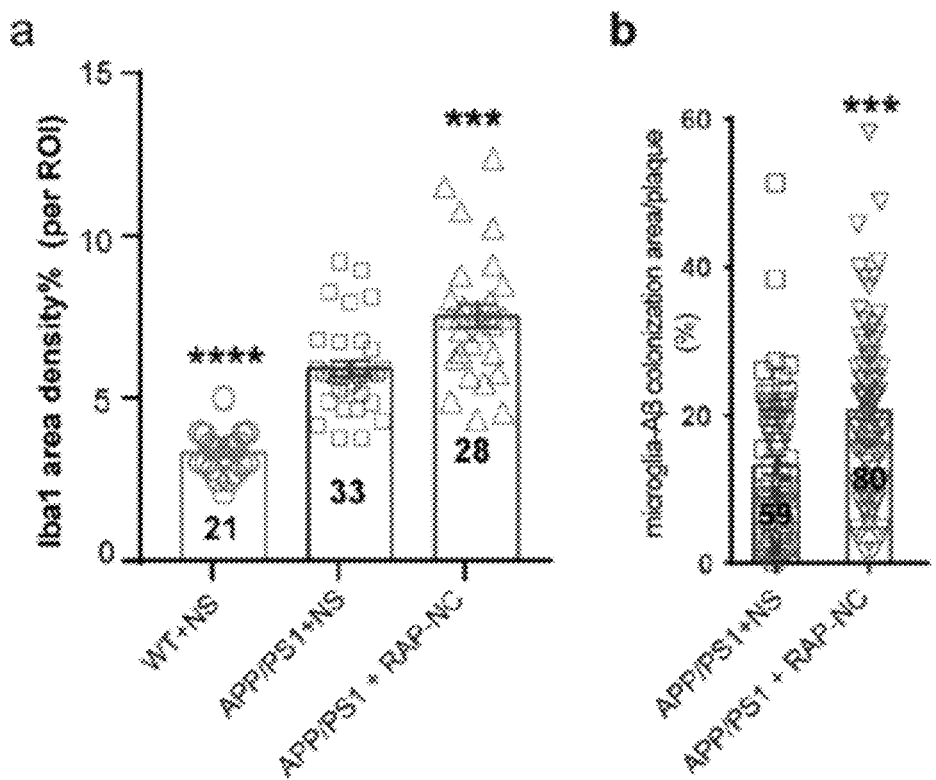
FIG. 12 shows that a targeted peptide-modified nano complex promotes uptake of Aβ plaques by microglial cells in the brain of AD model mice, wherein panel (a) shows an increase in microglial cells in the brain; panel (b) shows an increase in co-location of microglial cells and Aβ plaques; * represents $p<0.001$; and ** represents $p<0.0001$, indicating that there is a significant difference compared with a normal saline group.

Example 9. Promotion of Phagocytosis of Aβ Plaques by Microglial Cells in the Brain of AD Model Mice by a Targeted Peptide-Modified Nano Complex APP/PS1 mice were administered with a targeted peptide-modified nano complex, and then the brain thereof was taken, and AR plaques (a 6E10 antibody) and microglial cells (an Iba1 antibody) were immunostained as described in Example 8. The results showed that the targeted peptide-modified nano complex effectively increased the number of microglial cells and the uptake of AR plaques by microglial cells in the brain of AD model mice (FIG. 12).

Figure 13A:
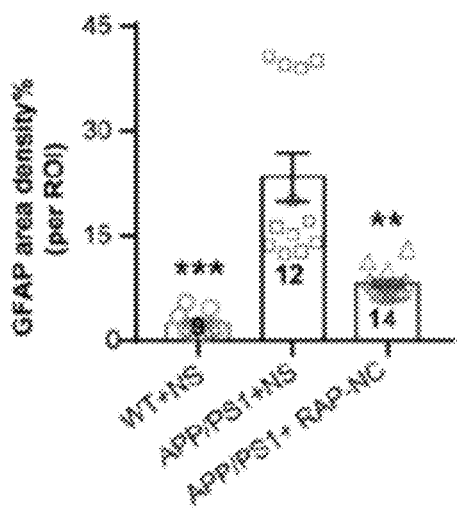
FIG. 13: panel (a) shows that a targeted peptide-modified nano complex alleviates activation of astrocytes in the brain of AD model mice, wherein * * represents $p<0.01$, and *** represents $p<0.001$, indicating that there is a significant difference compared with a normal saline group; panel (b) shows that a targeted peptide-modified nano complex promotes repair of the glymphatic system-associated transporter AQP4, near cerebral vessels of AD model mice (Scale bar: 25 μm).
Figure 13B:
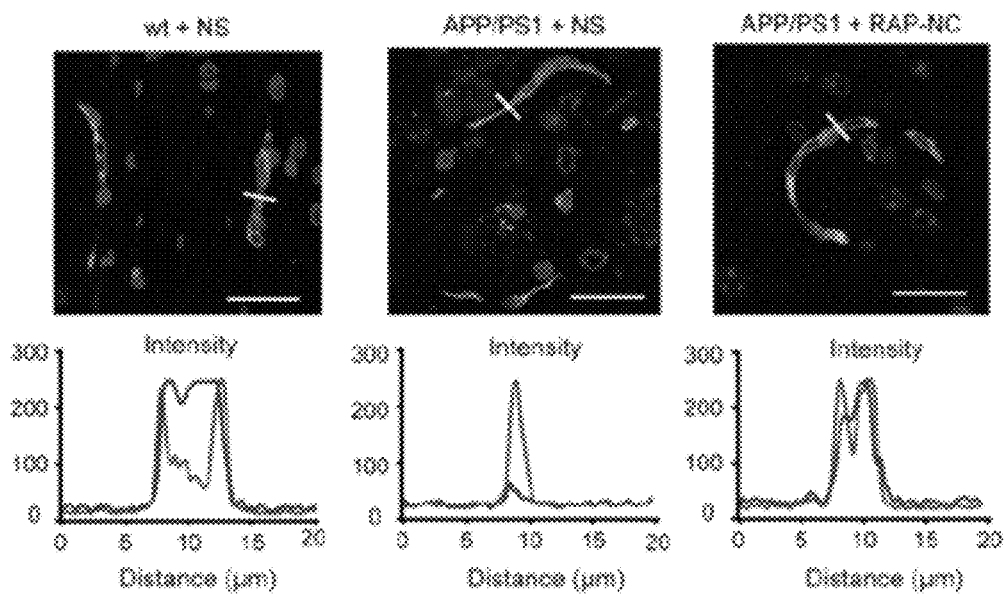

Example 10. Alleviation of Activation State of Astrocytes in the Brain of AD Model Mice and Promotion of Expression of Waste Removal-Related Proteins in Glymphatic System by a Targeted Peptide-Modified Nano Complex APP/PS1 mice were administered with a targeted peptide-modified nano complex for 4 weeks, and then the brain thereof was taken for being prepared into a section, and the activated astrocytes (a GFAP antibody) were immunostained and subjected to quantitative analysis as described in Example 7, indicating that the targeted peptide-modified nano complex effectively alleviated the activation state of astrocytes in the brain of AD model mice. In addition, an aquaporin transporter (AQP4) antibody was used to stain an intracerebral metabolic waste—transport and removal-associated protein AQP4 on the glymphatic system near cerebral vessels. Results indicated that the targeted peptide-modified nano complex effectively alleviated the waste removal capacity of the cerebral glymphatic system in AD model mice and promoted the functional recovery of the glymphatic system (FIG. 13).

Figure 14:
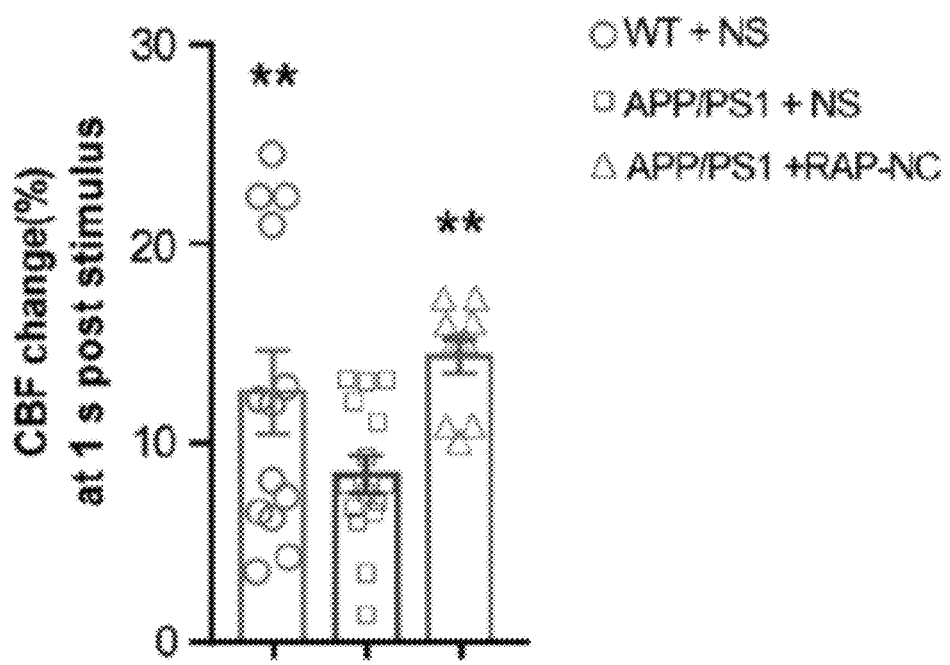
FIG. 14 shows that a targeted peptide-modified nano complex improves the neurovascular coupling response of cerebral blood flow in AD model mice: the figure shows the increase of blood flow in the corresponding response area of the brain —tubular cortex area at one second after beard electrical stimulation, wherein ** represents $p<0.01$, indicating that there is a significant difference compared with a normal saline group.

Example 11. Effective Repairing of the Cerebral Neurovascular Coupling Function in AD Model Mice by a Targeted Peptide-Modified Nano Complex Repairing of the cerebrovascular function and neurovascular unit components often leads to repairing of the neurovascular coupling function. APP/PS1 mice were administered with a targeted peptide-modified nano complex for 4 weeks, and then subjected to beard electrical stimulation, and the blood flow response of the corresponding brain tubular cortex area was observed in vivo as described in Example 7. The results showed that 1 s after stimulation, the relative cerebral blood flow response of a targeted peptide-modified nano complex treatment group was significantly higher than that of a normal saline group, indicating that the targeted peptide-modified nano complex effectively repaired the cerebral neurovascular coupling function of AD model mice (FIG. 14).

Figure 15A:
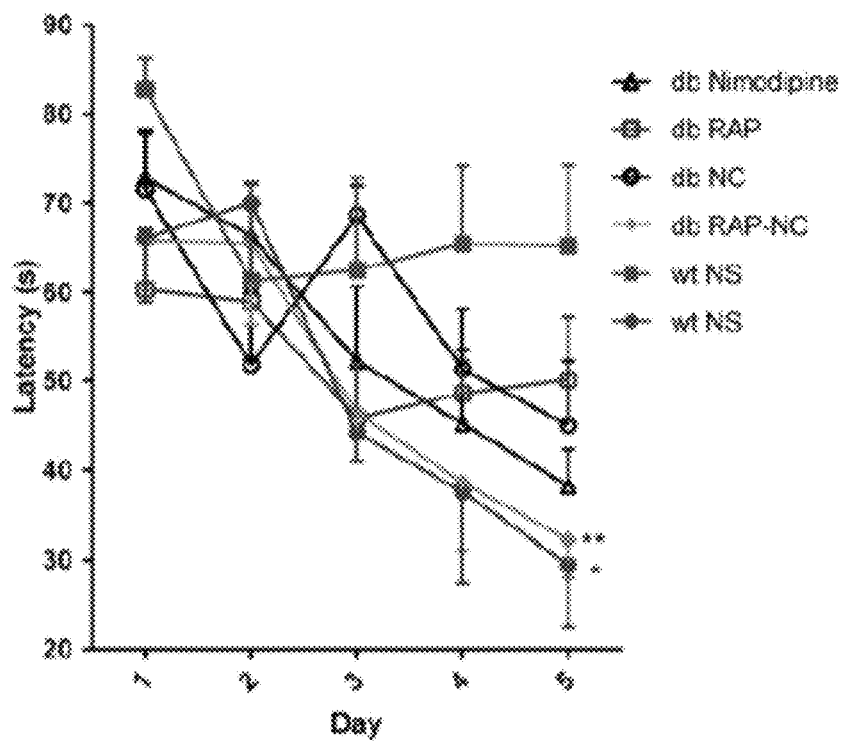
FIG. 15 shows that a targeted peptide-modified nano complex improves the cognitive function of diabetic encephalopathy model mice: panel (a) shows the improvement of swimming latency in a mouse water maze experiment, wherein * represents $p<0.05$, and ** represents $p<0.01$, indicating that there is a significant difference compared with a normal saline group; panel (b) shows increased platform crosses in a Morris water maze experiment; panel (c) shows the typical swimming trajectories of mice in each group, n=5-9.
Figure 15B:
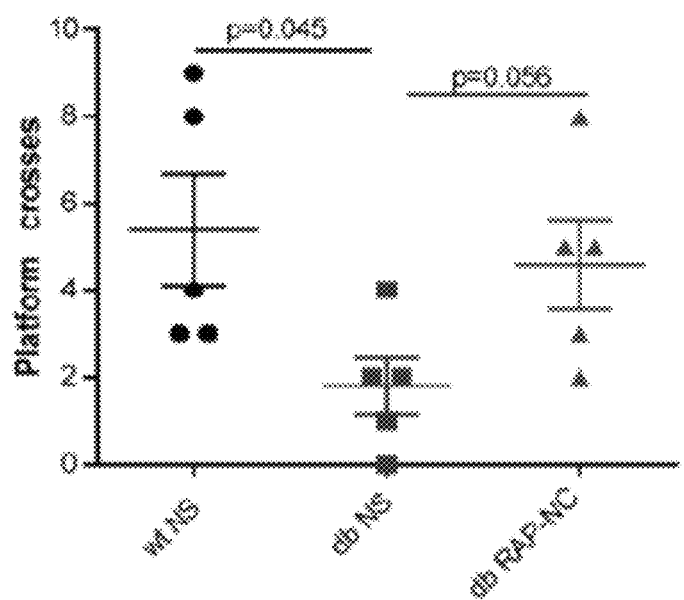
Figure 15C:
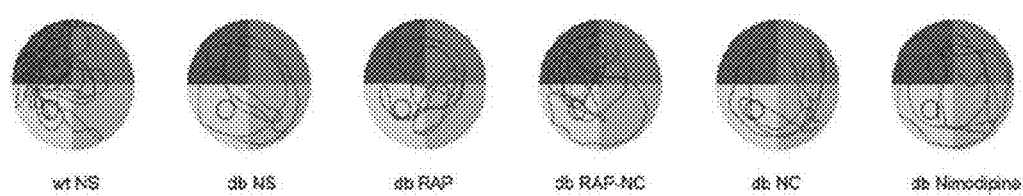

Example 12. Effective Repairing of the Cognitive Function in Diabetic Encephalopathy Model Mice by a Targeted Peptide-Modified Nano Complex Repairing of cerebral vessels and cerebral blood flow usually leads to improved cognitive function. Diabetic encephalopathy model mice (db) and littermate wild-type control mice (wt) were administered via tail veins with a targeted peptide-modified nano complex for 2 weeks, and then a water maze experiment was used to evaluate the spatial learning and memory ability of db mice as described in Example 8. The results showed that the targeted peptide-modified nano complex significantly improved the cognitive function in diabetic encephalopathy mice, which effect was better than that of a targeted peptide, a nano complex, and a calcium ion antagonist—nimodipine acting on the bloodstream alone (FIG. 15).

Figure 16A:
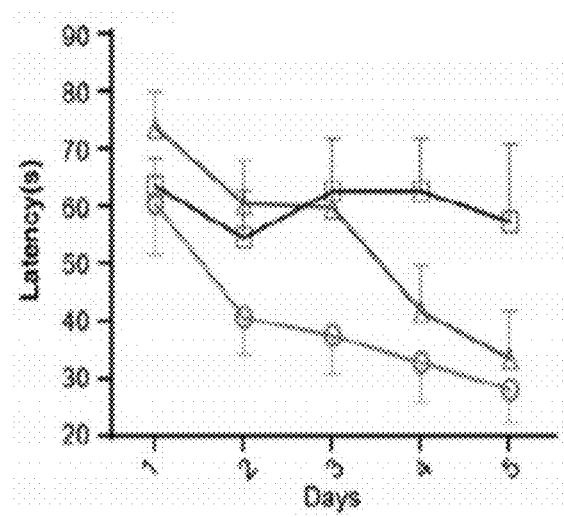
FIG. 16 shows that a targeted peptide-modified nano complex improves the cognitive function of AD model mice: panel (a) shows the improvement of swimming latency in a mouse Morris water maze experiment; panel (b) shows the increase of percentage of time in the platform in quadrant in a Morris water maze experiment, wherein * represents $p<0.05$, indicating that there is a significant difference compared with a normal saline group; panel (c) shows increased platform crosses, wherein * represents $p<0.05$, and ** represents $p<0.01$, indicating that there is a significant difference compared with a normal saline group, n=6-8.
Figure 16B:
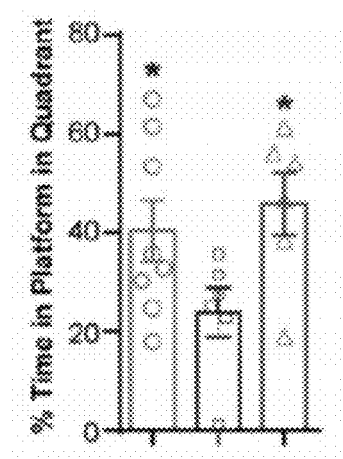
Figure 16C:
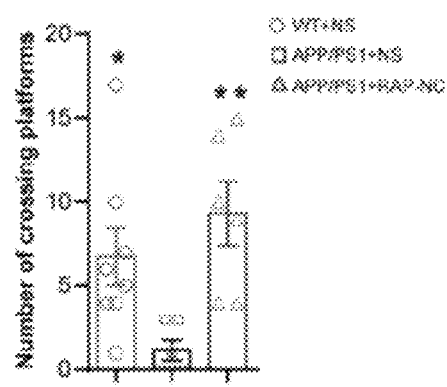

Example 13. Effective Repairing of the Cognitive Function in AD Model Mice by a Targeted Peptide-Modified Nano Complex Repairing of the cerebrovascular function and neurovascular coupling function usually leads to improved cognitive function. APP/PS1 mice were administered with a targeted peptide-modified nano complex for 4 weeks, and then a Morris water maze experiment was used to evaluate the spatial learning and memory ability of the mice as described in Example 11. The results showed that the targeted peptide-modified nano complex significantly improved the cognitive function of AD model mice, and had the efficacy of improving cognition and treating AD (FIG. 16).

Example 14. Effective Repairing of the Morphology and Function of Cerebral Vessels in Mice by a Targeted Peptide-Modified Nano Complex with miR-132-Loaded A targeted peptide-modified nano complex is of a biomimetic nano complex structure, which is adjustable. In addition to the fact listed in the above-mentioned examples that the structure itself is capable of repairing the neurovascular unit function, the structure can also carry a drug, such as a solid-phase core drug. Delivery of drugs to cerebrovascular lesion sites can be realized by preparing drugs such as RNA and DNA as solid-phase cores, and encapsulating the cores in the targeted peptide-modified nano complex, with microRNA-132 (miR-132) having a vascular regulation function as an example.

(1) Preparation

A calcium phosphate solid-phase core (which was miR-132 in this example) was prepared from a targeted peptide-modified protein with drug (such as nucleic acid)-loaded by an inverse microemulsion method. The inverse microemulsion was prepared by dispersing an aqueous solution in a cyclohexane oil phase solution containing nonylphenol polyoxyethylene ether. First, 300 μL of 2.5 M CaCl2) solution was dispersed in 20 mL of oil phase to form a uniformly dispersed water-in-oil inverse microemulsion. This step was the preparation of a calcium phase. A phosphorus phase was prepared by dispersing 300 μL of 12.5 mM Na2HPO4 solution in another 20 mL of oil phase, stirring the mixture for 10 min, and then adding 100 μL of 20 mg/mL 1,2-dioleoyl phosphatidic acid (DOPA) solution to the phosphorus phase. The two phases were uniformly dispersed, and then mixed and stirred for 45 min. The microemulsion reacted with each other after exchange, resulting in calcium phosphate precipitate. At this time, 40 mL of absolute ethanol was added to the above-mentioned mixed microemulsion for demulsification for 10 min. The mixture after demulsification was centrifuged at high speed (12,500 g) for about 20 min to remove excess surfactants and cyclohexane. After the same centrifugation operation was carried out three times, the precipitate obtained by centrifugation was the DOPA-modified calcium phosphate solid-phase core with miR-132-loaded, which was dispersed in 1 mL of chloroform and stored in a glass bottle. During preparation, 750 μL of calcium phosphate solid-phase core was added to a phospholipid solution, with the remaining steps being the same, as described in Example 1.

(2) Repairing Effect of a Targeted Peptide-Modified Nano Complex with miR-132-Loaded on Cerebral Vessels in Diabetic Encephalopathy Mice Diabetic encephalopathy mice (db) were administered with a targeted peptide-modified nano complex with miR-132-loaded for 2 weeks, and then the cerebral vessels were imaged by a multiphoton microscope as described in Example 8. The results showed that the targeted peptide-modified nano complex with miR-132-loaded effectively increased the cerebrovascular density in diabetic encephalopathy mice, and improved vascular fluidity and blood flow filling (FIG. 11).

Figure 17:
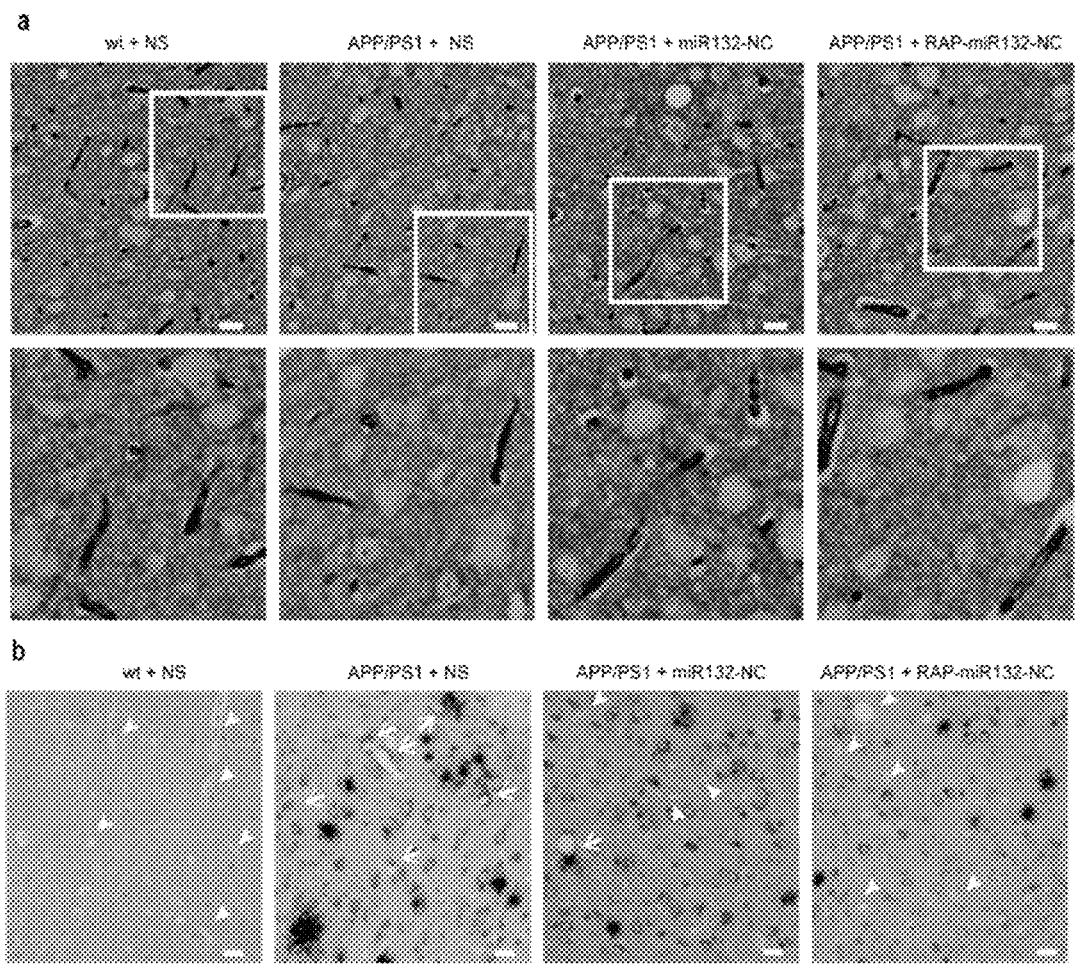
FIG. 17 shows that a targeted peptide-modified nano complex with miR-132-loaded improves the cerebrovascular morphology and the expression of glucose transporter 1 (Glut1) on cerebral vessels (a) and promotes removal of AR near cerebral vessels (b) in AD model mice (Scale bar for panel a: 20 μm; Scale bar for panel b: 20 μm).

(3) Repairing Effect of a Targeted Peptide-Modified Nano Complex with miR-132-Loaded on Cerebral Vessels in AD Model Mice APP/PS1 mice were administered via tail veins with a targeted peptide-modified nano complex with miR-132-loaded for 4 weeks, and then the brain thereof was taken for being prepared into a section to show the glucose transporter (GLUT1) on cerebral vessels and the Aβ plaques near the cerebral vessels, as described in Example 8. The results showed that the targeted peptide-modified nano complex with miR-132-loaded promoted restoration of the vascular morphology to be normal and smooth, restoration of the lumen to be smooth and full, uniform distribution of the GLUT1 positive region on the vascular wall, and transport of the brain energy substrate glucose to the brain. Moreover, the targeted peptide-modified nano complex with miR-132-loaded promoted the removal of the AR plaques near the blood vessels and alleviated cerebrovascular amyloidosis. It showed that the targeted peptide-modified nano complex with miR-132-loaded effectively promoted the repairing of cerebrovascular morphology and transport function (inward transport of energy and outward transport of metabolic wastes) (FIG. 17).

Figure 18:
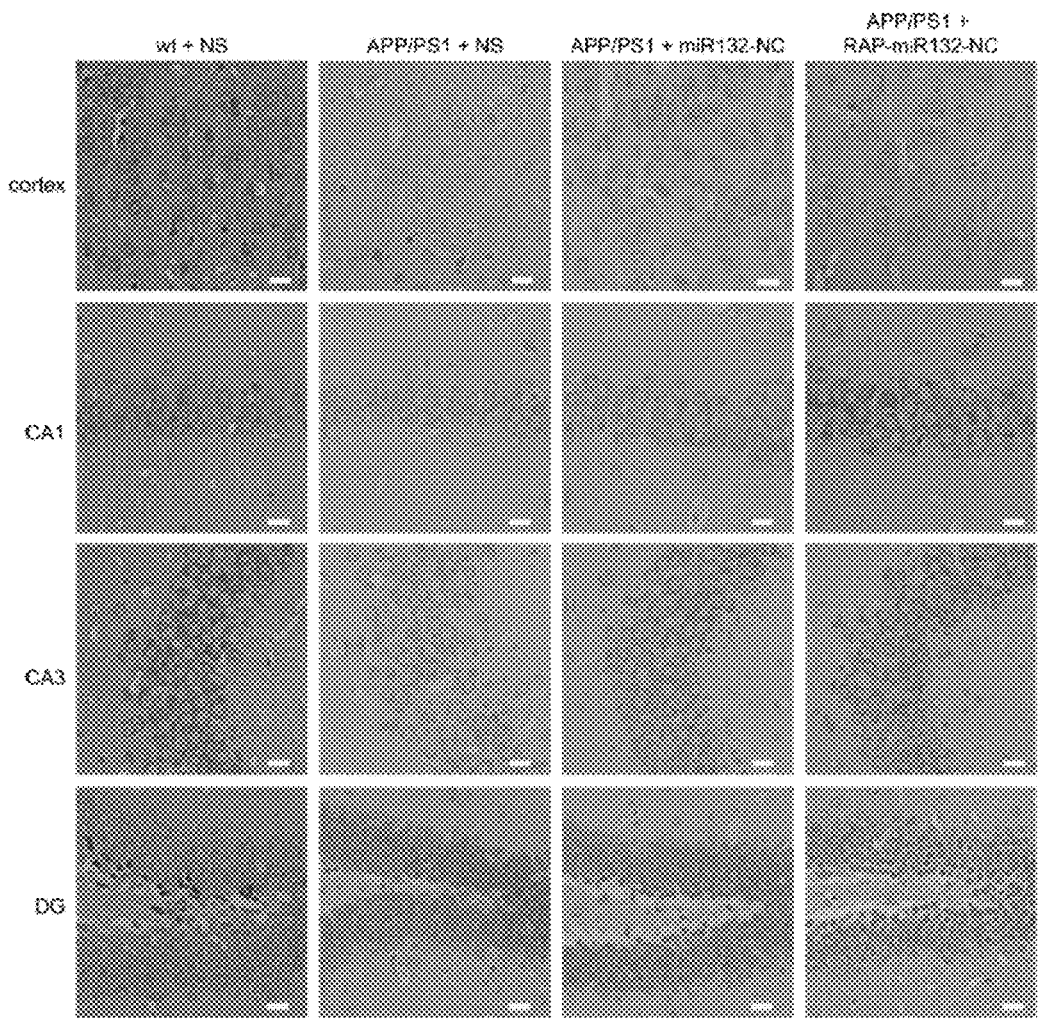
FIG. 18 shows that a targeted peptide-modified nano complex with miR-132-loaded repairs neurons in the brain of AD model mice (Nissl staining) (Scale bar: 20 μm).

Example 15. Effective Neuron Repair in the Brain of AD Model Mice with a Targeted Peptide-Modified Nano Complex with miR-132 Loaded APP/PS1 mice were administered via tail veins with a targeted peptide-modified nano complex loaded with miR-132, and then the brain thereof was taken for being prepared into a section to Nissl stain neurons in the cerebral cortex and the hippocampus region, as described in Example 14. The results showed that the neurons in the targeted peptide-modified nano complex group loaded with miR-132 restored full cell morphology, clear intracellular Nissl body morphology and thickness of the neuronal cell body layer in the hippocampus region, indicating that the nano complex effectively promoted neuron repair. (FIG. 18).

Example 16. Good Preliminary Safety of a Targeted Peptide-Modified Nano Complex

Figure 19:
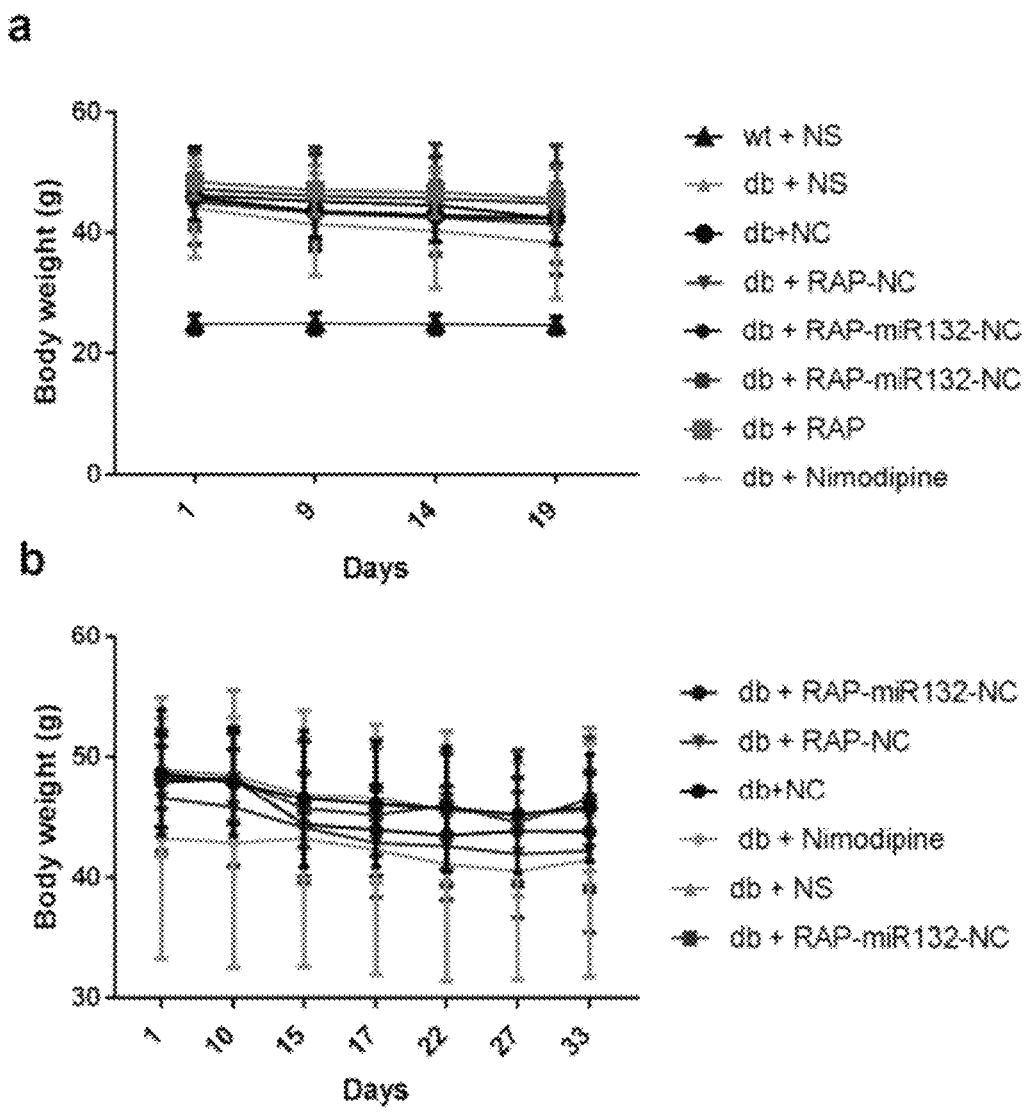
FIG. 19 shows that the drug has a relatively low toxicity: panel (a) shows that administration of a targeted peptide-modified nano complex and a targeted peptide-modified nano complex with miR-132-loaded has no significant effect on the body weight of wild-type (wt) and diabetic encephalopathy (db) mice, n=6-8; panel (b) shows that administration of a targeted peptide-modified nano complex and a targeted peptide-modified nano complex with miR-132-loaded has no significant effect on the body weight of wild-type (wt) and AD model (APP/PS1) mice, n=6-8.

Both diabetic encephalopathy and AD are chronic diseases, which usually take a long time of drug administration and require treatment strategies with good safety. The results showed that during administration to db mice and APP/PS1 mice, the mice were in good condition, with no significant changes in diet, drinking water, and hair smoothness, and the body weight thereof fluctuated slightly within a certain range without significant changes (FIG. 19), indicating that the targeted peptide-modified nano complex and the structure with drug-loaded thereof are less toxic.

Figure 20:
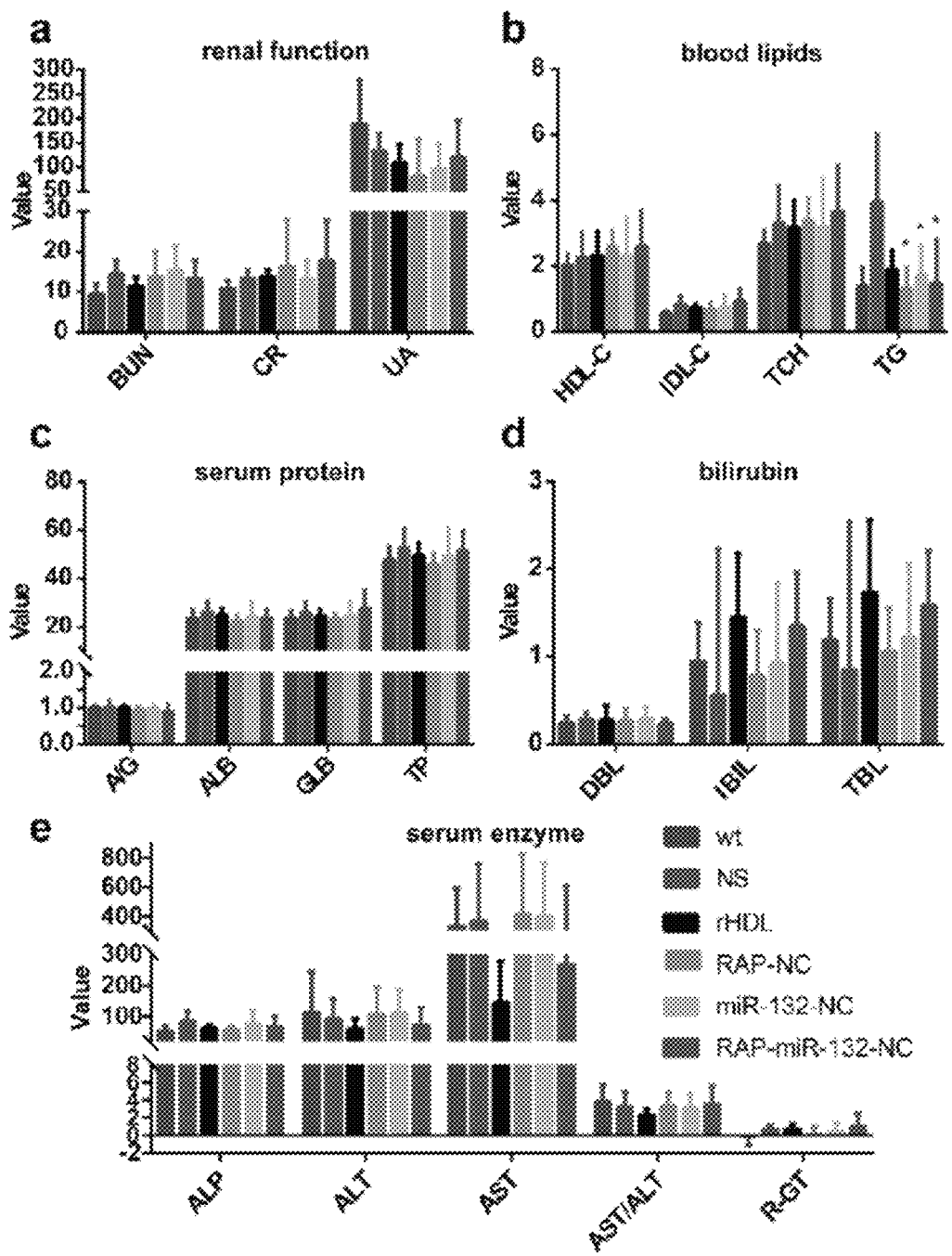
FIG. 20 shows that administration of a targeted peptide-modified nano complex and a targeted peptide-modified nano complex with miR-132-loaded has no significant toxicity to diabetic encephalopathy mice. Serum biochemical indicators include (a) renal function (BUN, urea; CR, creatinine; UA, uric acid), (b) blood lipids (HDL-C, high-density nano complex cholesterol; LDL-C, low-density nano complex cholesterol; TCH, total cholesterol; TG, triglycerides), (c) serum proteins (A/G, albumin/globulin ratio; ALB, albumin; GLB, globulin; TP, total protein), (d) bilirubin (DBL, direct bilirubin; IBIL, indirect bilirubin; TBL, total bilirubin), and (e) serum enzymes (ALP, alkaline phosphatase; ALT, alanine aminotransferase; AST, aspartate aminotransferase; AST/ALT, aspartate aminotransferase/alanine aminotransferase), n=3.

After four weeks of administration, APP/PS1 mice were measured for serum biochemical indicators, including renal function, blood lipids, serum proteins, bilirubin (liver function) and serum enzymes (liver function). The results showed that the targeted peptide-modified nano complex and the targeted peptide-modified nano complex loaded with miR-132 significantly reduced serum triglycerides and promoted transition of the blood lipids to a healthier level, whereas other indicators did not change significantly, indicating that the above-mentioned two targeted peptide-modified nano complexes had no obvious hepatotoxicity and had good safety (FIG. 20).

The above are only the preferred embodiments of the present disclosure. It should be noted that for those of ordinary skill in the art, several improvements and modifications can be made without departing from the principle of the present disclosure, and these improvements and modifications are also be regarded as the scope of protection of the present disclosure.

What is claimed is:

1. A nano complex for targeted repairing of a neurovascular lesion,
wherein the nano complex comprises a lipid, an apolipoprotein and a targeted peptide, and the targeted peptide is formed by covalently linking, by means of a bridge structure, a nanocarrier linking end and a peptide chain which targets RAGE, which specifically binds to a cerebrovascular lesion site, wherein
the targeted peptide comprises one or more of:
AC-Phe-Ala-Glu-Lys-Phe-Lys-Glu-Ala-Val-Lys-Asp-Tyr-Phe-Ala-Lys-Phe-Trp-Asp-Gly-Ser-Gly-Glu-Leu-Lys-Val-Leu-Met-Glu-Lys-Glu-Leu (R4, SEQ ID NO. 1);
AC-Phe-Ala-Glu-Lys-Phe-Lys-Glu-Ala-Val-Lys-Asp-Tyr-Phe-Ala-Lys-Phe-Trp-Asp-Gly-Gly-Glu-Leu-Lys-Val-Leu-Met-Glu-Lys-Glu-Leu (R1, SEQ ID NO. 2);
AC-Phe-Ala-Glu-Lys-Phe-Lys-Glu-Ala-Val-Lys-Asp-Tyr-Phe-Ala-Lys-Phe-Trp-Asp-Ile-Ala-Glu-Leu-Lys-Val-Leu-Met-Glu-Lys-Glu-Leu (R2, SEQ ID NO. 3);
AC-Phe-Ala-Glu-Lys-Phe-Lys-Glu-Ala-Val-Lys-Asp-Tyr-Phe-Ala-Lys-Phe-Trp-Asp-Ile-Gly-Glu-Leu-Lys-Val-Leu-Met-Glu-Lys-Glu-Leu (R3, SEQ ID NO. 4);
AC-Phe-Ala-Glu-Lys-Phe-Lys-Glu-Ala-Val-Lys-Asp-Tyr-Phe-Ala-Lys-Phe-Trp-Asp-Ile-Ala-Ile-Glu-Leu-Lys-Val-Leu-Met-Glu-Lys-Glu-Leu (R5, SEQ ID NO. 5);
AC-Phe-Ala-Glu-Lys-Phe-Lys-Glu-Ala-Val-Lys-Asp-Tyr-Phe-Ala-Lys-Phe-Trp-Asp-Gly-Ala-Gly-Ala-Glu-Leu-Lys-Val-Leu-Met-Glu-Lys-Glu-Leu (R6, SEQ ID NO. 6);
AC-Phe-Ala-Glu-Lys-Phe-Lys-Glu-Ala-Val-Lys-Asp-Tyr-Phe-Ala-Lys-Phe-Trp-Asp-Gly-Gly-Ser-Gly-Gly-Glu-Leu-Lys-Val-Leu-Met-Glu-Lys-Glu-Leu (R7, SEQ ID NO. 7); and
AC-Phe-Ala-Glu-Lys-Phe-Lys-Glu-Ala-Val-Lys-Asp-Tyr-Phe-Ala-Lys-Phe-Trp-Asp-Gly-Ser-Ser-Ser-Gly-Gly-Glu-Leu-Lys-Val-Leu-Met-Glu-Lys-Glu-Leu (R8, SEQ ID NO. 8).

2. The nano complex for targeted repairing of a neurovascular lesion according to claim 1, wherein the targeted peptide has a sequence as shown in any one of AC-Phe-Ala-Glu-Lys-Phe-Lys-Glu-Ala-Val-Lys-Asp-Tyr-Phe-Ala-Lys-Phe-Trp-Asp-Gly-Ser-Gly-Glu-Leu-Lys-Val-Leu-Met-Glu-Lys-Glu-Leu (R4, SEQ ID NO. 1), AC-Phe-Ala-Glu-Lys-Phe-Lys-Glu-Ala-Val-Lys-Asp-Tyr-Phe-Ala-Lys-Phe-Trp-Asp-Gly-Gly-Glu-Leu-Lys-Val-Leu-Met-Glu-Lys-Glu-Leu (R1, SEQ ID NO. 2), AC-Phe-Ala-Glu-Lys-Phe-Lys-Glu-Ala-Val-Lys-Asp-Tyr-Phe-Ala-Lys-Phe-Trp-Asp-Ile-Ala-Ile-Glu-Leu-Lys-Val-Leu-Met-Glu-Lys-Glu-Leu (R5, SEQ ID NO. 5), or AC-Phe-Ala-Glu-Lys-Phe-Lys-Glu-Ala-Val-Lys-Asp-Tyr-Phe-Ala-Lys-Phe-Trp-Asp-Gly-Ala-Gly-Ala-Glu-Leu-Lys-Val-Leu-Met-Glu-Lys-Glu-Leu (R6, SEQ ID NO. 6).

3. The nano complex for targeted repairing of the neurovascular lesion according to claim 1, wherein the lipid is one or more of lecithin, soybean phospholipid, phosphatidylcholine, phosphatidylserine, phosphatidylglycerol, phosphatidic acid, cardiolipin, ceramide, cerebroside, ganglioside, glyceride and a derivative thereof.

4. The nano complex for targeted repairing of the neurovascular lesion according to claim 3, wherein the lipid is monosialotetrahexosyl ganglioside.

5. The nano complex for targeted repairing of the neurovascular lesion according to claim 1, wherein the molar ratio of the targeted peptide to the lipid is 1:10 to 1:500.

6. A method for preparing the nano complex for targeted repairing of the neurovascular lesion according to claim 1, wherein the method comprises the following steps:
a) synthesizing the targeted peptide according to claim 1 by using a solid-phase peptide synthesis method;
b) preparing a lipid by using a conventional method, including a film hydration method, an extrusion method and a continuous flow chip method;
c) firstly adding the targeted peptide to the lipid prepared in b), and then adding an apolipoprotein thereto, wherein the molar ratio of the targeted peptide to the lipid is 1:10 to 1: 500 to prepare a targeted peptide-modified nano complex.

7. A method for treating cognitive impairment, which comprises administering the nano complex for targeted repairing of the neurovascular lesion according to claim 1 to a patient.

8. The method for treating cognitive impairment according to claim 7, wherein the cognitive impairment is Alzheimer's disease and diabetic encephalopathy.

9. A method for the preparation of a cerebrovascular lesion-targeted drug delivery system with drug-loaded, which comprises employing the nano complex for targeted repairing of the neurovascular lesion according to claim 1.

10. The method for the preparation of a cerebrovascular lesion-targeted drug delivery system with drug-loaded according to claim 9, wherein the loaded drug is a drug for treating cognitive impairment.

11. A targeted peptide for modifying the nano complex for targeted repairing of the neurovascular lesion, wherein the targeted peptide has a sequence as shown in any one of AC-Phe-Ala-Glu-Lys-Phe-Lys-Glu-Ala-Val-Lys-Asp-Tyr-Phe-Ala-Lys-Phe-Trp-Asp-Gly-Ser-Gly-Glu-Leu-Lys-Val-Leu-Met-Glu-Lys-Glu-Leu (R4, SEQ ID NO. 1), AC-Phe-Ala-Glu-Lys-Phe-Lys-Glu-Ala-Val-Lys-Asp-Tyr-Phe-Ala-Lys-Phe-Trp-Asp-Gly-Gly-Glu-Leu-Lys-Val-Leu-Met-Glu-Lys-Glu-Leu (R1, SEQ ID NO. 2), AC-Phe-Ala-Glu-Lys-Phe-Lys-Glu-Ala-Val-Lys-Asp-Tyr-Phe-Ala-Lys-Phe-Trp-Asp-Ile-Ala-Ile-Glu-Leu-Lys-Val-Leu-Met-Glu-Lys-Glu-Leu (R5, SEQ ID NO. 5), or AC-Phe-Ala-Glu-Lys-Phe-Lys-Glu-Ala-Val-Lys-Asp-Tyr-Phe-Ala-Lys-Phe-Trp-Asp-Gly-Ala-Gly-Ala-Glu-Leu-Lys-Val-Leu-Met-Glu-Lys-Glu-Leu (R6, SEQ ID NO. 6), and the nano complex further comprises a lipid and an apolipoprotein.

12. A method for the preparation of a cerebrovascular lesion-targeted drug delivery system with drug-loaded, which comprises employing the targeted peptide for modifying the nano complex for targeted repairing of the neurovascular lesion according to claim 11.

13. A method for treating cognitive impairment, which comprises administering the targeted peptide for modifying the nano complex for targeted repairing of the neurovascular lesion according to claim 11 to a patient.

14. The method for treating cognitive impairment according to claim 13, wherein the cognitive impairment is Alzheimer's disease and diabetic encephalopathy.

15. The nano complex for targeted repairing of the neurovascular lesion according to claim 1, wherein the molar ratio of the targeted peptide to the lipid is 1:30.

16. The method according to claim 6, wherein the molar ratio of the targeted peptide to the lipid is 1:30.

17. The method for the preparation of a cerebrovascular lesion-targeted drug delivery system with drug-loaded according to claim 9, wherein the cognitive impairment is Alzheimer's disease and diabetic encephalopathy.

* * * * *

SEQUENCE LISTING

<160> NUMBER OF SEQ ID NOS: 8

<210> SEQ ID NO 1
<211> LENGTH: 31
<212> TYPE: PRT
<213> ORGANISM: Artificial Sequence
<220> FEATURE:
<223> OTHER INFORMATION: Targeted peptide containing a bridge structure
      peptide segment for linking a nanocarrier linking end and a
      peptide chain which targets diseased blood vessels

<400> SEQUENCE: 1

Phe Ala Glu Lys Phe Lys Glu Ala Val Lys Asp Tyr Phe Ala Lys Phe
1               5                   10                  15

Trp Asp Gly Ser Gly Glu Leu Lys Val Leu Met Glu Lys Glu Leu
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Targeted peptide containing a bridge structure
      peptide segment for linking a nanocarrier linking end and a
      peptide chain which targets diseased blood vessels

<400> SEQUENCE: 2

Phe Ala Glu Lys Phe Lys Glu Ala Val Lys Asp Tyr Phe Ala Lys Phe
1               5                   10                  15

Trp Asp Gly Gly Glu Leu Lys Val Leu Met Glu Lys Glu Leu
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Targeted peptide containing a bridge structure
      peptide segment for linking a nanocarrier linking end and a
      peptide chain which targets diseased blood vessels

<400> SEQUENCE: 3

Phe Ala Glu Lys Phe Lys Glu Ala Val Lys Asp Tyr Phe Ala Lys Phe
1               5                   10                  15

Trp Asp Ile Ala Glu Leu Lys Val Leu Met Glu Lys Glu Leu
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Targeted peptide containing a bridge structure
      peptide segment for linking a nanocarrier linking end and a
      peptide chain which targets diseased blood vessels

<400> SEQUENCE: 4

Phe Ala Glu Lys Phe Lys Glu Ala Val Lys Asp Tyr Phe Ala Lys Phe
1               5                   10                  15

Trp Asp Ile Gly Glu Leu Lys Val Leu Met Glu Lys Glu Leu
            20                  25                  30

<210> SEQ ID NO 5
<211> LENGTH: 31
<212> TYPE: PRT
<213> ORGANISM: Artificial Sequence

```
<220> FEATURE:
<223> OTHER INFORMATION: Targeted peptide containing a bridge structure
      peptide segment for linking a nanocarrier linking end and a
      peptide chain which targets diseased blood vessels

<400> SEQUENCE: 5

Phe Ala Glu Lys Phe Lys Glu Ala Val Lys Asp Tyr Phe Ala Lys Phe
1               5                   10                  15

Trp Asp Ile Ala Ile Glu Leu Lys Val Leu Met Glu Lys Glu Leu
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Targeted peptide containing a bridge structure
      peptide segment for linking a nanocarrier linking end and a
      peptide chain which targets diseased blood vessels

<400> SEQUENCE: 6

Phe Ala Glu Lys Phe Lys Glu Ala Val Lys Asp Tyr Phe Ala Lys Phe
1               5                   10                  15

Trp Asp Gly Ala Gly Ala Glu Leu Lys Val Leu Met Glu Lys Glu Leu
            20                  25                  30

<210> SEQ ID NO 7
<211> LENGTH: 33
<212> TYPE: PRT
<213> ORGANISM: Artificial Sequence
<220> FEATURE:
<223> OTHER INFORMATION: Targeted peptide containing a bridge structure
      peptide segment for linking a nanocarrier linking end and a
      peptide chain which targets diseased blood vessels

<400> SEQUENCE: 7

Phe Ala Glu Lys Phe Lys Glu Ala Val Lys Asp Tyr Phe Ala Lys Phe
1               5                   10                  15

Trp Asp Gly Gly Ser Gly Gly Glu Leu Lys Val Leu Met Glu Lys Glu
            20                  25                  30

Leu

<210> SEQ ID NO 8
<211> LENGTH: 34
<212> TYPE: PRT
<213> ORGANISM: Artificial Sequence
<220> FEATURE:
<223> OTHER INFORMATION: Targeted peptide containing a bridge structure
      peptide segment for linking a nanocarrier linking end and a
      peptide chain which targets diseased blood vessels

<400> SEQUENCE: 8

Phe Ala Glu Lys Phe Lys Glu Ala Val Lys Asp Tyr Phe Ala Lys Phe
1               5                   10                  15

Trp Asp Gly Ser Ser Ser Gly Gly Glu Leu Lys Val Leu Met Glu Lys
            20                  25                  30

Glu Leu
```